(12) United States Patent
Lenihan et al.

(10) Patent No.: US 7,185,411 B2
(45) Date of Patent: Mar. 6, 2007

(54) METHOD AND APPARATUS FOR FORMING FINE GAUGE AND MONOFILAMENT SINGLE AND DOUBLE-ARMED SUTURES

(75) Inventors: Timothy P. Lenihan, Morrisville, PA (US); Demarest D. David, Parsippany, NJ (US)

(73) Assignee: Ethicon, Inc., Somerville, NJ (US)

( * ) Notice: Subject to any disclaimer, the term of this patent is extended or adjusted under 35 U.S.C. 154(b) by 386 days.

(21) Appl. No.: 10/768,811

(22) Filed: Jan. 30, 2004

(65) Prior Publication Data
US 2005/0166384 A1  Aug. 4, 2005

(51) Int. Cl.
*B23P 19/04* (2006.01)
*B23P 21/00* (2006.01)

(52) U.S. Cl. ............... 29/433; 29/771; 29/505; 29/517; 29/564.6; 29/33 K; 29/33 R; 29/712; 29/715; 29/788; 163/5

(58) Field of Classification Search ............. 29/433, 29/505, 515, 516, 517, 564.6, 564.7, 705, 29/711, 712, 715, 788, 771, 33 R, 33 K, 29/33 J, 33 P; 163/5
See application file for complete search history.

(56) References Cited

U.S. PATENT DOCUMENTS

| | | | |
|---|---|---|---|
| 4,922,904 A * | 5/1990 | Uetake et al. | 606/226 |
| 5,438,746 A | 8/1995 | Demarest et al. | |
| 5,473,810 A * | 12/1995 | Demarest et al. | 29/712 |
| 5,485,668 A * | 1/1996 | Demarest et al. | 29/517 |
| 5,487,212 A * | 1/1996 | Demarest et al. | 29/407.05 |
| 5,487,308 A | 1/1996 | Demarest et al. | |
| 5,495,420 A * | 2/1996 | Demarest et al. | 700/117 |
| 5,500,991 A * | 3/1996 | Demarest et al. | 29/407.08 |
| 5,608,962 A * | 3/1997 | Colligan et al. | 29/517 |
| 5,793,634 A | 8/1998 | Demarest et al. | |
| 5,844,142 A | 12/1998 | Blanch et al. | |
| 5,903,966 A * | 5/1999 | Sonderegger | 29/464 |

(Continued)

OTHER PUBLICATIONS

"Improved System and Method for Sensing Variations in a Strand", U.S. Appl. No. 10/683,497 filed Oct. 10, 2003, Inventor: David Demarest, et al.

*Primary Examiner*—Essama Omgba

(57) ABSTRACT

An apparatus for forming armed sutures has a swaging station for receiving, holding and swaging needles that are deposited therein. A linear motor drives a suture insertion gripper, which pulls suture from a supply reel and inserts a cut end thereof into a needle held in the swaging station. A ganged needle transfer assembly with a plurality of spaced needle gripper units carries needles along a line substantially at right angles to the suture line and transfers them to and from the swaging station and other needle processing stations. A precisor orients needles prior to placement in the swaging station and a pull test assembly tests armed sutures in both destructive and non-destructive modes. Both ends of the production line may be automated, e.g., by robots which load and offload needles prior to and after swaging, respectively. The apparatus is capable of forming double armed sutures by using a rotatable mount for the suture insertion gripper and a secondary, loop gripper. A suture transfer gripper extending up to the suture from a multi-tiered stack of slide tables. The suture transfer gripper cooperates with the suture insertion and loop grippers to hold the suture during cutting, insertion and transfer to the pull test apparatus and thereby protects the suture during processing.

37 Claims, 19 Drawing Sheets

U.S. PATENT DOCUMENTS

| | | | |
|---|---|---|---|
| 5,911,449 A * | 6/1999 | Daniele et al. ............. 29/33 K |
| 5,915,751 A * | 6/1999 | Esteves et al. ................ 29/783 |
| 5,918,284 A | 6/1999 | Blanch et al. |
| 5,937,504 A | 8/1999 | Esteves et al. |
| 5,943,759 A * | 8/1999 | Shikakubo et al. ........... 29/517 |
| 5,943,765 A * | 8/1999 | Shikakubo et al. ........... 29/705 |
| 6,012,216 A * | 1/2000 | Esteves et al. ............. 29/564.7 |
| 6,058,821 A | 5/2000 | Demarest et al. |
| 6,076,255 A * | 6/2000 | Shikakubo et al. ........... 29/715 |
| 6,081,981 A * | 7/2000 | Demarest et al. ........ 29/407.08 |
| 6,115,650 A * | 9/2000 | Demarest et al. ........... 700/259 |
| 6,163,948 A * | 12/2000 | Esteves et al. ................ 29/517 |
| 6,263,558 B1 | 7/2001 | Blanch et al. |

\* cited by examiner

METHOD AND APPARATUS FOR FORMING FINE GAUGE AND MONOFILAMENT SINGLE AND DOUBLE-ARMED SUTURES

FIELD OF THE INVENTION

The present invention relates to apparatus for automatically swaging needles, such as surgical needles, to a suture, and more particularly, to an apparatus that produces armed sutures using very fine gauge needles and suture and also has the capacity to make double-armed sutures.

BACKGROUND OF THE INVENTION

Methods and apparatus for preparing single and double armed sutures are known as exemplified by U.S. Pat. Nos. 6,263,558, 6,058,821, 5,937,504 and 5,438,746. Improvements and variations are desirable, however, to facilitate preparing armed sutures having specific characteristics. For example, it would be desirable for an apparatus for fabricating armed sutures to be proficient in preparing double-armed sutures and in producing armed sutures using sutures and needles of a very fine gauge and/or with monofilament suture.

SUMMARY OF THE INVENTION

The limitations of prior art methods and apparatus for making armed sutures are addressed by the present invention, which includes an apparatus for forming armed sutures, having a swaging station for receiving, holding and swaging needles that are deposited therein. A suture insertion apparatus inserts suture into needles held in the swaging station; and acts along a first line. The suture insertion apparatus moves an end of the suture to be inserted along the first line from a starting position to an ending position where the end of the suture is inserted in the suture hole of a needle. A needle transfer assembly for carrying needles to and from the swaging station, acts along a second line substantially perpendicular to the first line, with the first line and the second line intersecting at the swage station.

BRIEF DESCRIPTION OF THE FIGURES

FIGS. 19, 19A, 20 and 20A are plan and associated enlarged views of the suture cutter of the present invention in the retracted and extended positions, respectively.

DETAILED DESCRIPTION OF THE INVENTION

Figure 27:
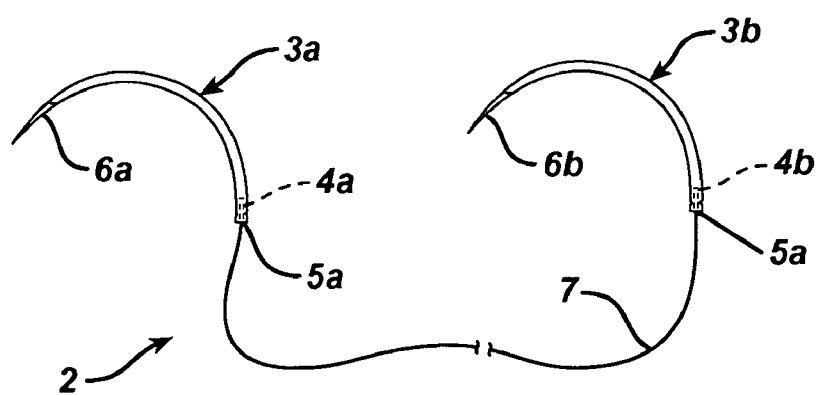
FIG. 27 is a perspective view of a double-armed suture.

Methods and apparatus for automated production of armed sutures are known. e.g., as shown in U.S. Pat. Nos. 6,263,558, 6,058,821, 5,937,504 and 5,438,746, each of which are owned by the present Assignee and are incorporated herein for their teachings concerning the preparation and manufacture of armed sutures. Each of these patents describes methods and apparatus wherein a needle, e.g., 3a (see FIG. 27) having a suture hole 4a in the blunt end 5a distal to point 6a is held in a swaging die. Suture material 7 is grasped by a gripper and drawn off a spool of suture material. The suture 7 is cut to provide a free end thereof which may be inserted into the suture hole 4a of the needle 3a. After insertion of the suture 7 into the suture hole, 4a, a swaging die operating on the blunt end 5a is forced inwardly, crimping the suture hole 4a around the suture 7 and causing the needle 3a to grip the suture 7. A cutter then cuts the suture distal to the needle 3a to a selected length. This process is repeated automatically to produce multiple single-armed sutures. As shown in FIG. 27, a needle 3b may be attached to the other end of the suture 7 to form a double-armed suture 2. When automated processes are used for making armed sutures with very fine suture material, the requirements for precision are increased greatly, e.g., it is much more difficult to align the cut end of the suture material with the needle hole 4a to enable insertion. Since the suture material 7 is thinner, it is easier to injure or cut it inadvertently, using the same forces that would not injure thicker suture material. For very fine gauge sutures, monofilament suture material is frequently utilized. Monofilament suture is generally less flexible and less resilient to perpendicular deformations and therefore is more prone to be deformed, cut or broken when subjected to shearing forces. Often, the needles used with fine gauge sutures are laser-drilled without a chamfered opening. This type of opening increases the difficulty associated with inserting ("threading") the suture 7 into the suture hole 4a. The present invention, while useful for forming armed sutures from multi-stranded material and from material of any gauge, is particularly well suited to using small gauge, monofilament suture material and for forming double-armed sutures 2. Hereafter, where it is not significant which needle 3a, 3b or their related points 4a, 4b is referred to, e.g., when referring to a needle of a single armed suture, the reference number without distinguishing letter will be used. For example, "needle 3" shall refer to either of needles 3a or 3b, which are interchangeable.

Figure 1:
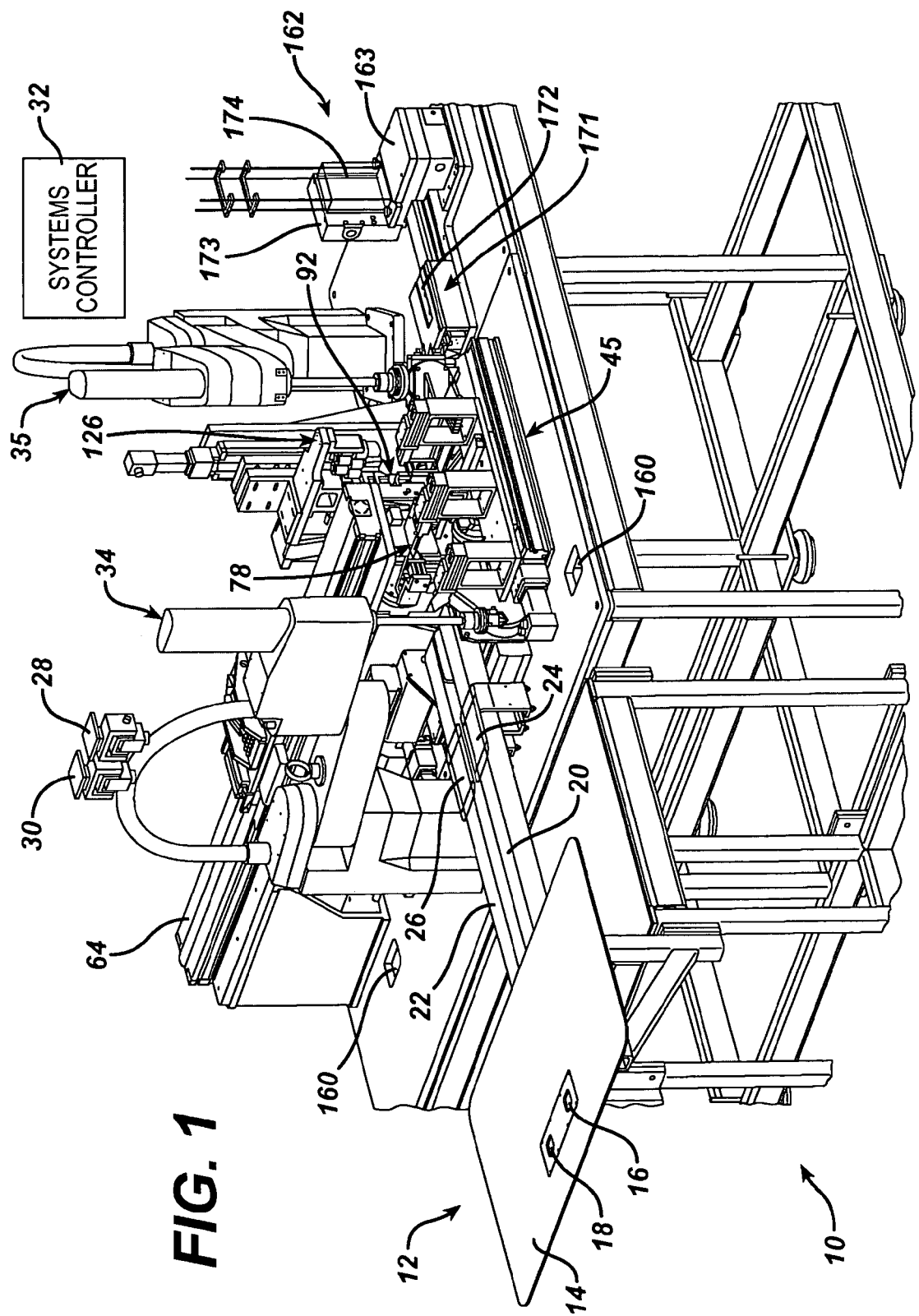
FIG. 1 is a perspective view of a system for fabricating armed sutures in accordance with an embodiment of the present invention.
Figure 2:
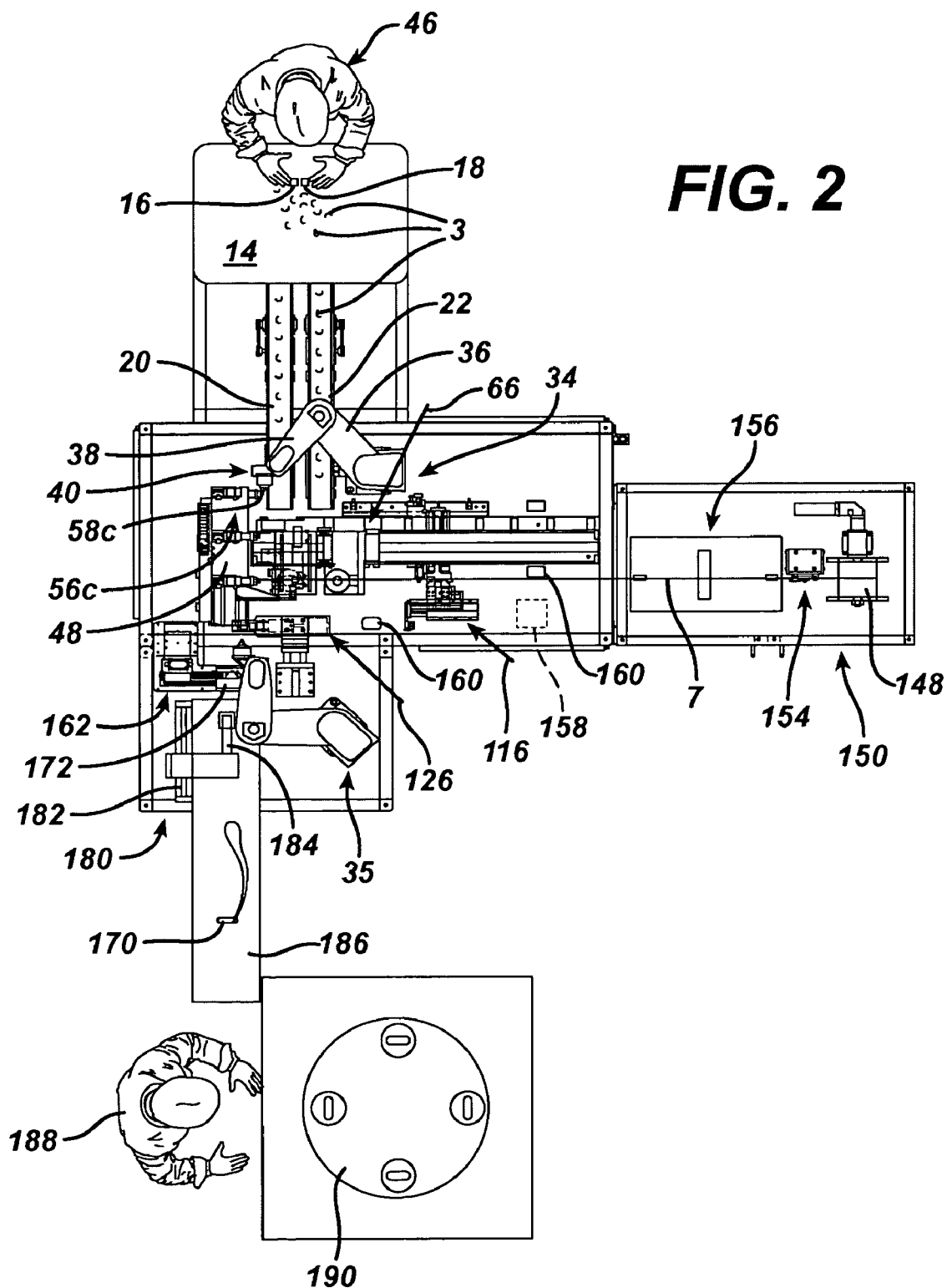
FIG. 2 is a plan view of the system of FIG. 1.

FIGS. 1 and 2 show a system 10 in accordance with the present invention for forming single and double-armed sutures 2, and including an in-feed station 12 with a needle sorting table 14. The needle sorting table 14 has first and second needle orifices 16 and 18 that align with first and second needle in-feed conveyors 20, 22 positioned under the needle sorting table 14. Conveyors 20 and 22 may be made from a translucent material and may be back-lit in areas 24 and 26. First and second optical sensors 28, 30 are juxtaposed above the back-lit sections 24, 26 of the conveyors 20, 22 for sensing the presence of needles 3 (see FIG. 2) on the conveyors. Needles 3 will be attached to suture material 7 to form single or double-armed sutures 2. Optical information from sensors 28, 30 is relayed to a systems controller 32 which programmatically controls a needle in-feed robot 34, such as an Adept® robot unit, (available from Adept Technology, Incorporated of Livermore, Calif.) permitting the robot 34 to retrieve needles 3 from the conveyors 20, 22. While the system controller 32 is depicted as a single unit for ease of illustration, the digital controls for the system 10 may include additional subsystems. For example, a Programmable Logic Controller (PLC), such as a Siemens® S7-300 could be utilized for overall control (Siemens Corporation of New York, N.Y.). The PLC would work in conjunction with a personal computer (PC) programmed to provide a graphical user interface. A motion controller, such as a Parker®/Compumotor® 6K8 (available from Parker Hannifin Corporation of Rohnert Park, Calif.) may intermediate between the PLC and servo drives utilized to move and activate components of the system 10. The PLC may also be used to direct robotic controllers to control the in-feed robot 34, as well as the out-feed robot 35 which retrieves armed sutures 2 from the system, as described hereafter.

Figure 3:
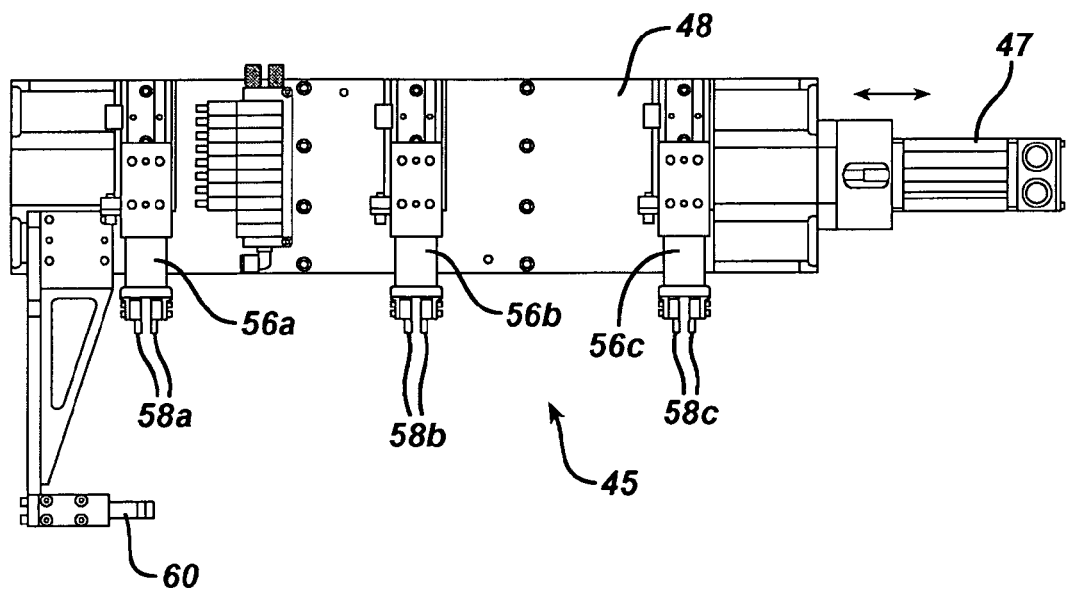
FIGS. 3 and 4 are plan and front views, respectively, of a needle transfer assembly of the system shown in FIGS. 1–2.
Figure 4:
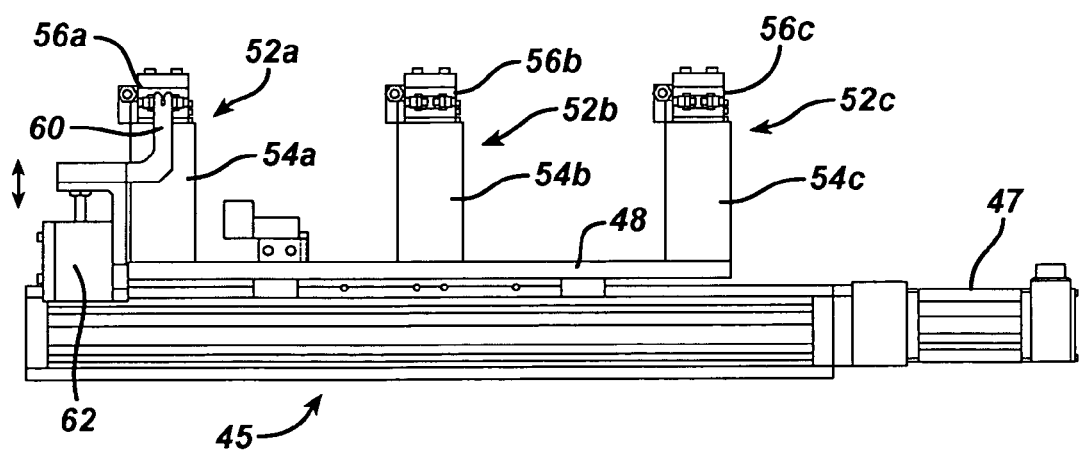
Figure 5:
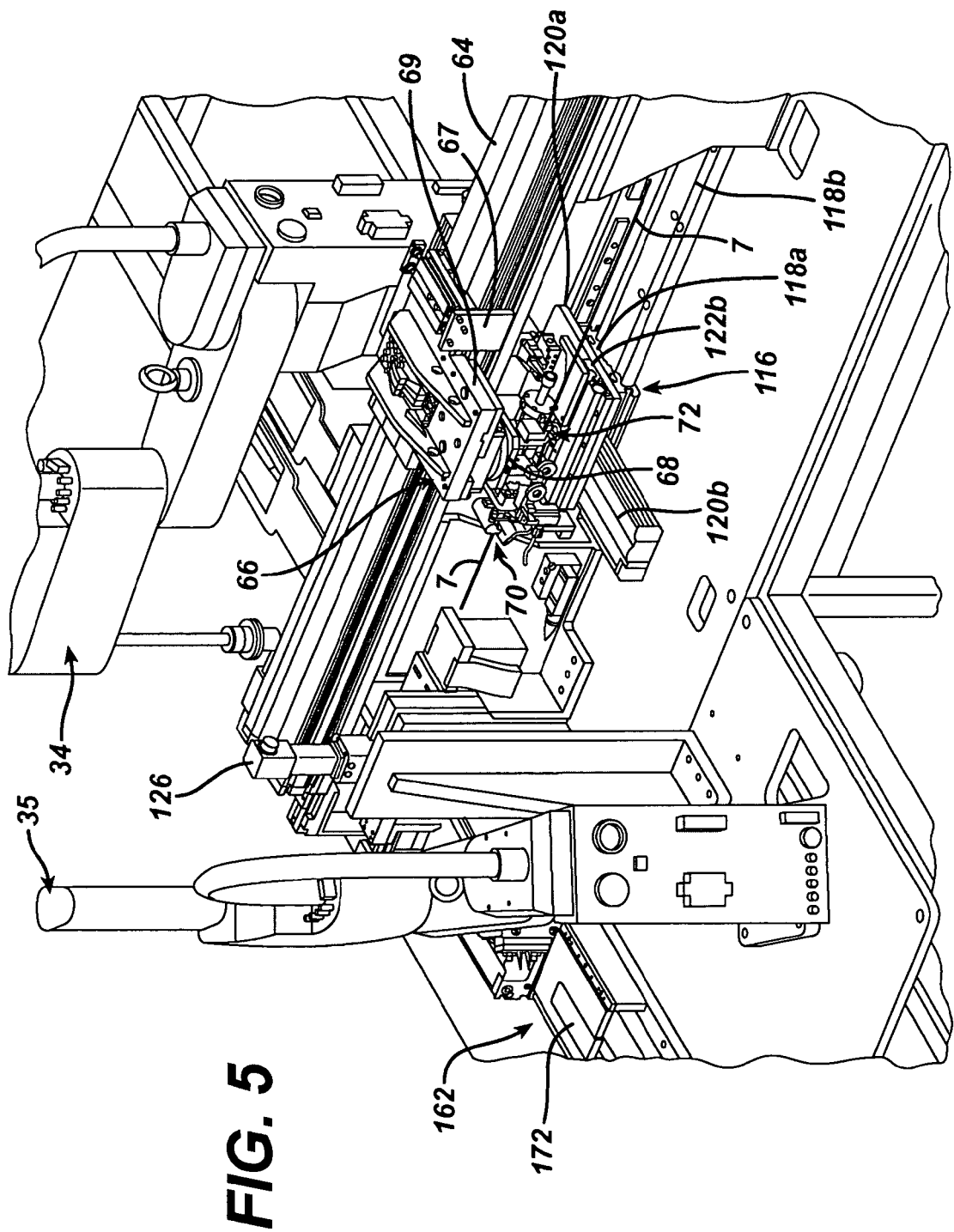
FIG. 5 is a perspective view of the system of FIG. 1 from another perspective.

As shown in FIG. 2, and described at length below in reference to FIGS. 23–26, the in-feed robot 34 (and the out-feed robot 35) has articulating arms 36, 38 and a rotatable end-effector 40 with specially adapted needle gripper fingers 42 (42a, 42b) that are used to grasp needles 3 that are sensed by the optical sensors 28, 30. The in-feed robot 34 grasps the needles 3 from the conveyors 20, 22 and passes them to needle gripping fingers 58c of gripper unit 56c (see FIGS. 3 and 4), for further processing. As can be appreciated in FIG. 2, a human operator 46 separates the needles 3 on the needle sorting table 14 and drops the needles through the needle orifices 16 and 18 onto the conveyors 20, 22 in a spaced manner to enable the optical sensors 28, 30 to discern individual needles 3, enabling the controller 32 to direct the in-feed robot 34 to remove them and pass them to needle gripper unit 56c on the needle transfer assembly (walking beam assembly) 45. As shown more clearly in FIGS. 3 and 4, a linear actuator 47 (screw-type or linear motor) of the needle transfer assembly 45 controls the lateral position of a gripper table 48. The gripper table 48 supports three needle gripper assemblies 52a, 52b, 52c, each having a spacer 54a–c and a slide-mounted gripper unit 56a, 56b, 56c assembled thereon. The slide-mounted gripper units 56a–c are extensible and retractable under pneumatic control in a direction perpendicular to the displacement direction of the gripper table 48 as controlled by linear actuator 47. Each of the gripper units 56a–c has a pair of needle gripping fingers 58a–c which can be selectively placed in an opened position and a closed position. In FIG. 3, all gripper units 56a–c are in the extended position (with the respective gripper fingers 58a–c in an open position.) In the closed position, the needle gripping fingers 58a–c are capable of gripping and retaining a needle 3 therein. The gripper table 48 also supports a suture transfer guide 60, the elevation of which is controlled by a pneumatic cylinder 62, for controlling suture position during the fabrication of double-armed sutures, as described further below. The spacing between the gripper units 56a–c corresponds to the spacing between successive processing stages of the system 10, viz., needle in-feed 12, precisor 78, swaging 92 and pull test 126 (See FIGS. 2 and 22). This arrangement permits the simultaneous sideways transfer of three needles 3 from one processing stage to a subsequent processing stage (where the needles 3 are then deposited for processing) by executing one sideways shift of the gripper table 48. A return shift of the gripper table 48 positions the needle transfer assembly 45 to execute another simultaneous advancement of a group of three needles. As noted above, the gripper units 56a–c extend and retract toward/away from the various processing stages (12, 78, 92 and 126) to retrieve or deposit a needle from/at that stage. In transferring a needle 3 from one processing stage to another, the transferring gripper, e.g., the needle gripper fingers 42 of the in-feed robot 34 are clamped onto the needle 3 and the receiving gripper fingers, e.g., 58c are open to receive the needle 3. The receiving gripper 56c is extended. The needle 3 is positioned within the open gripper fingers 58c of the receiving gripper unit 56c and they are closed to grip the needle 3. Once gripped by the receiving gripper fingers 58c, the transferring gripper fingers 42 open, releasing their grip on the needle 3. The gripper unit 56c then retracts and is shifted to laterally due to the linear actuator 47 moving the gripper table 48. The gripper unit 56c then extends toward the processing stage in front of which it is juxtaposed, viz., the precisor 78, to deposit the needle 3 it is carrying at that processing stage and, in so doing, executes a "needle transfer" type motion. All of the gripper units 56a–c on the gripper table 48 execute the same type of needle transfer actions simultaneously. Needles 3 are thereby moved simultaneously from the needle in-feed station 12 to the precisor station 78 (by gripper unit 56c), from the precisor station 78 to the swage station 92 (by gripper unit 56b) and from the swage station 92 to the pull test station 126 (by gripper unit 56a). Having considered the mechanism that the system 10 uses for transfer of needles 3, the apparatus for controlling and moving suture will now be described in conjunction with FIGS. 5–8 and 16–18.

Figure 6:
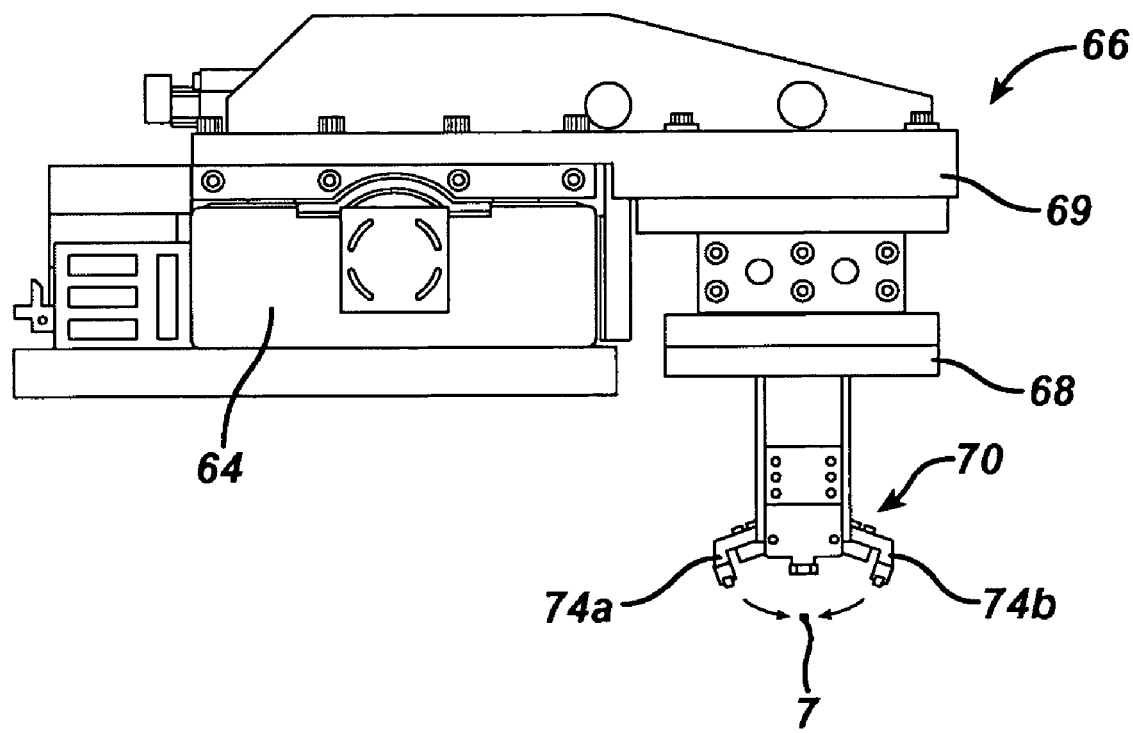
FIGS. 6–8 are front, side and plan views, respectively, of a suture tower of the system shown in FIGS. 1–5.
Figure 7:
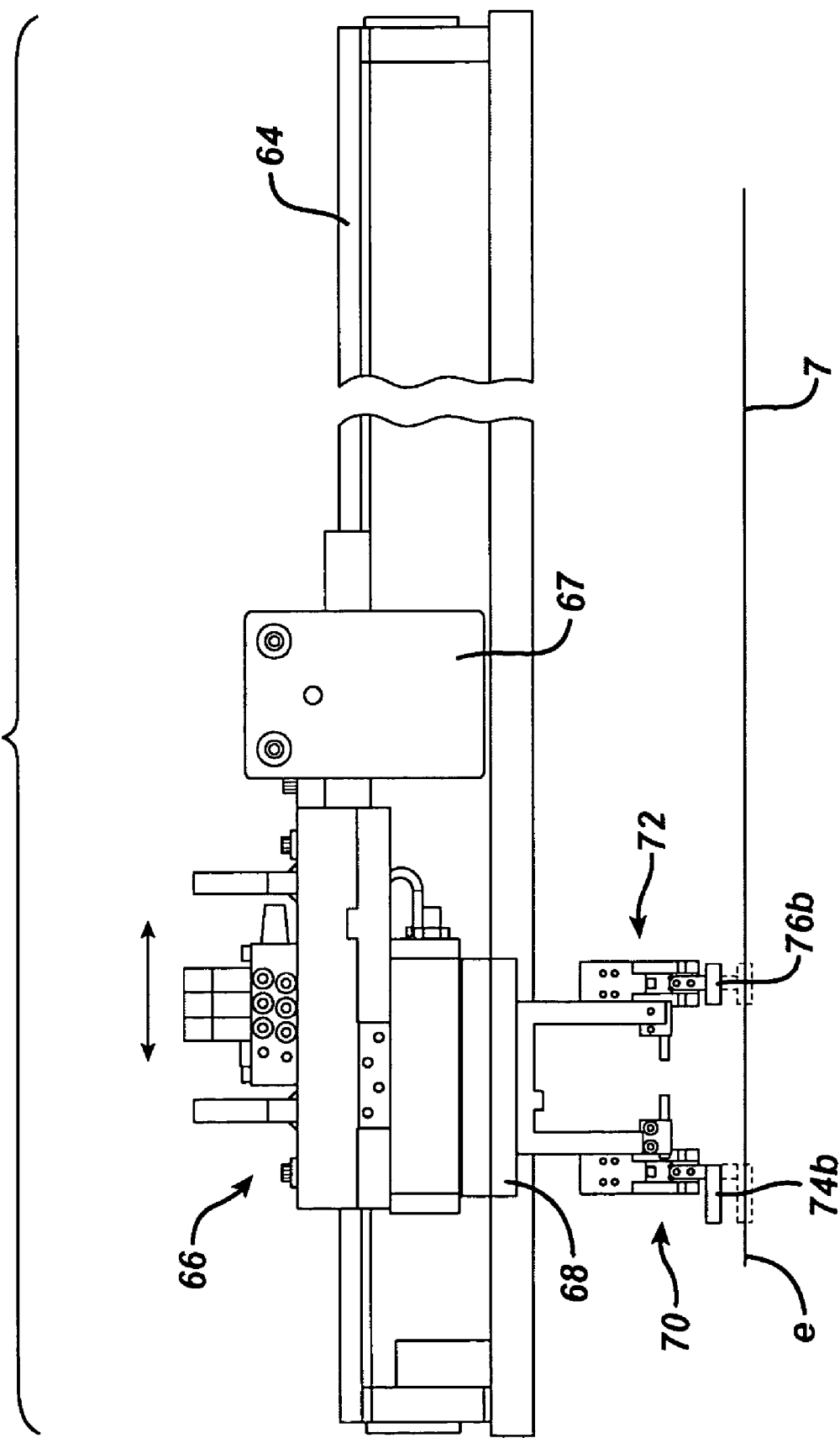
Figure 8:
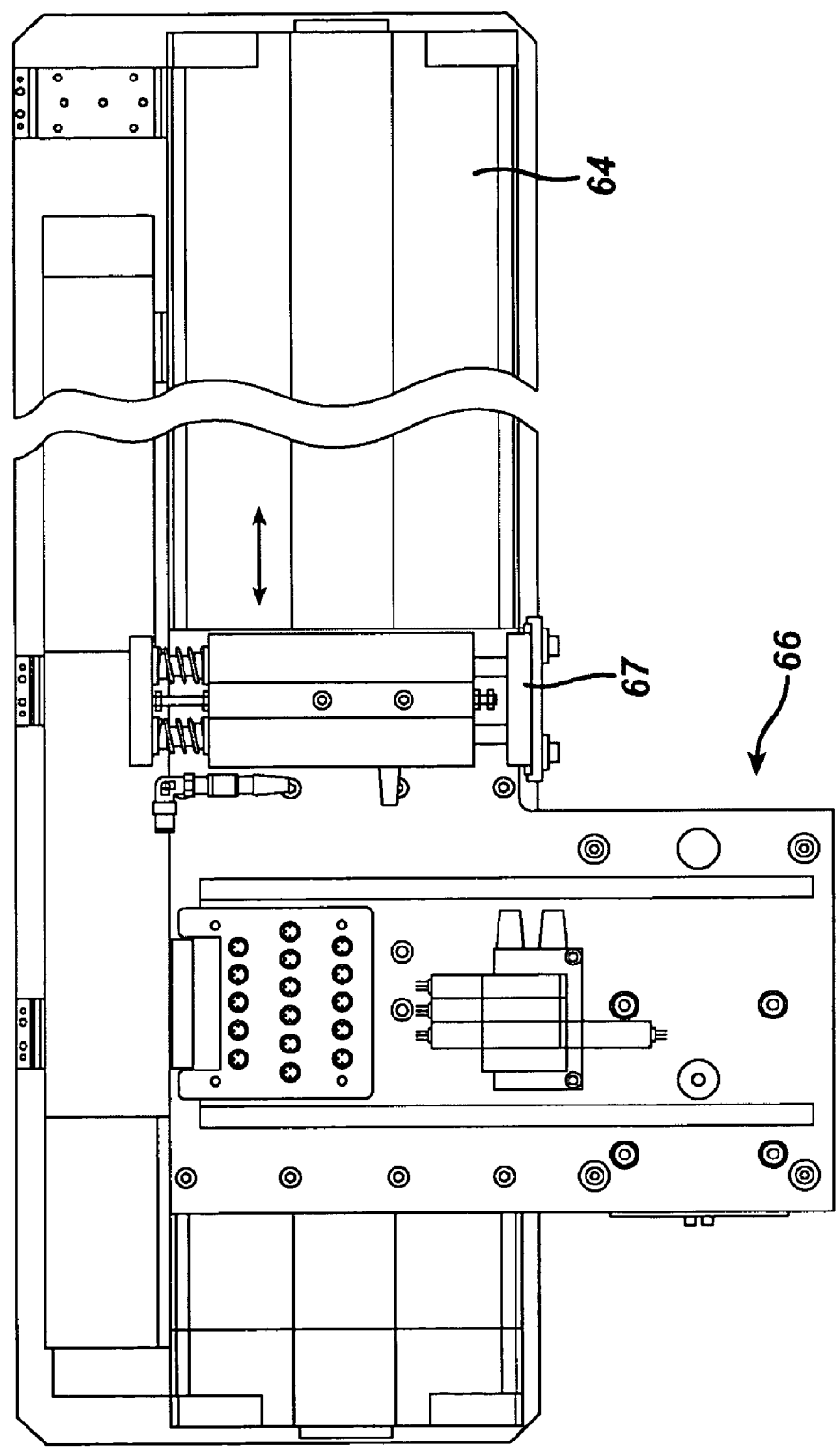
Figure 9:
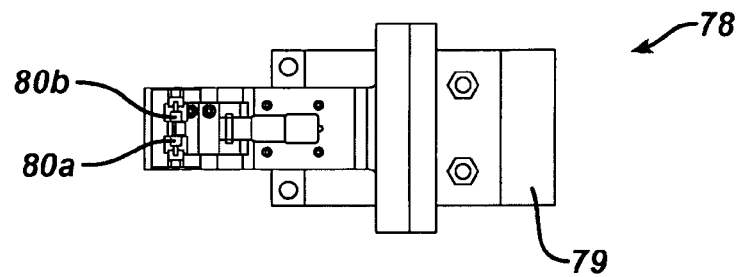
FIGS. 9–11 are plan, front and side views, respectively, of a precisor of the system shown in FIGS. 1–8.
Figure 10:
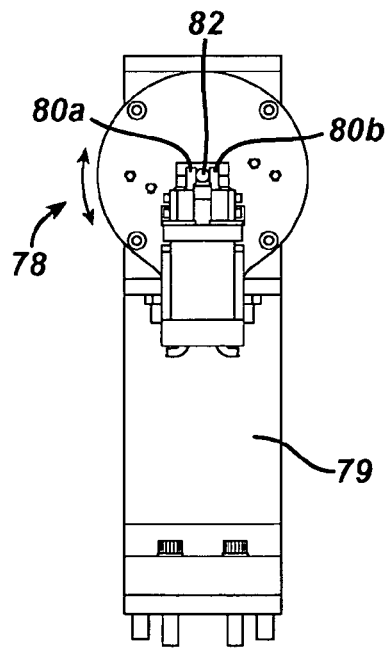

The prime mover of the suture 7 is the suture tower assembly 66 which is driven along a line of travel extending between a forward position to a rearward position (see FIG. 7) by a linear motor 64. A pair of pneumatic grippers (a suture insertion gripper 70 and a loop gripper 72) are carried on a rotatable turret 68 (having the ability to rotate 180 degrees) suspended from a slide carriage 69 of the suture tower assembly 66. The linear motor 64 slidably supports and controls the position of the suture tower assembly 66. Once the linear motor 64 positions the suture tower assembly 66 at a selected position, a pneumatically controlled brake 67 may be applied to retain it in that position. Suture grippers 70, 72, each have a pair of opposed suture gripping fingers 74a, 74b and 76a, 76b, respectively, with an opened position and a closed position. (The opened position is shown in FIG. 6 and the closed position is shown in dotted lines in FIG. 7.) The opened and closed positions of the suture gripping fingers 74a, 74b and 76a, 76b are independently controlled, so that fingers 74a, 74b can be closed while fingers 76a, 76b are open and vice versa. Alternatively, both sets of gripping fingers 74a, 74b, 76a and 76b can be closed and opened simultaneously. As shown in FIG. 7, suture gripping fingers 74a and 74b extend asymmetrically toward the swage station 92 to aid in placing a free end of the suture 7 into a needle hole of a needle held in the swage station 92. More particularly, the suture insertion gripper fingers 74a, 74b have an "L" shape. In FIG. 7, the bottom leg of the "L" points towards the front of the system 10.

The basic run sequence for advancing the suture 7 for single-armed sutures, is that suture insertion gripper 70 grasps the suture 7 which is extended along a line substantially as shown in FIG. 7 and the suture 7 is cut, leaving a free end e. The suture tower assembly 66 is moved in a forward direction (toward swage station 92) and the free end (cut end) e of the suture 7 is inserted into the suture hole 4 of a needle 3 held in the swage station 92. As the suture tower assembly 66 is advanced toward the swage station 92, suture 7 is payed out by a suture pay-out system 150 to maintain proper suture tension at the selected payout rate. A suture transfer gripper 124 extending up from a stacked slide assembly 116 (both of which shall be described below in reference to FIGS. 16–18) then grips the suture 7 distal to the free end e at a point about an inch less than the length of the finished armed suture 2 (measured from the needle 3). The needle 3 is then swaged by the swage station 92, fixing the suture 7 therein, whereupon the suture insertion gripper 70 releases its grip on the suture 7 and the suture tower assembly 66 moves rearwardly to a point about an inch further from the needle 3 than the finished length of the suture 7, and the suture insertion gripper 70 grips the suture 7 again. At this point, the suture 7 is held by the needle 3 clamped in the swage station 92, by the suture transfer gripper 124, which is positioned, e.g., 25 inches from the needle 3, and by the suture insertion gripper 70, positioned, e.g., 27 inches from the needle 3. A cutter assembly 128 (see FIG. 19) similar in structure and operation to that shown in U.S. Pat. Nos. 6,058,821 and 6,263,558 then cuts the suture 7 between the transfer gripper 124 and the insertion gripper 70.

Figure 11:
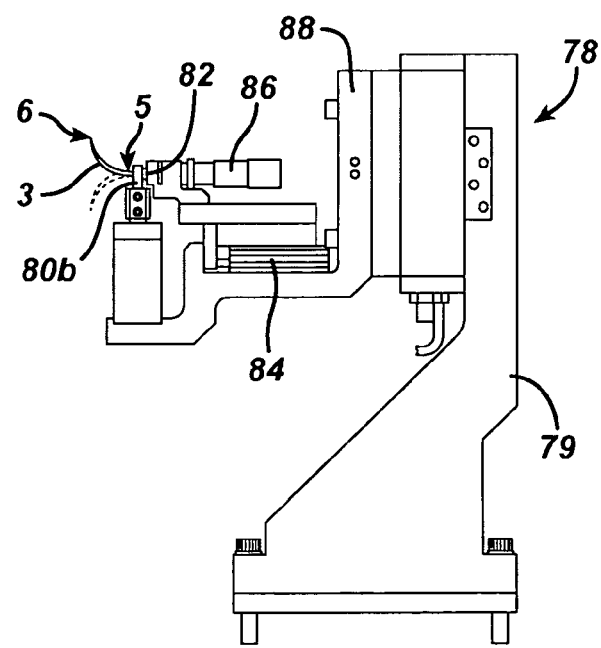
Figure 12:
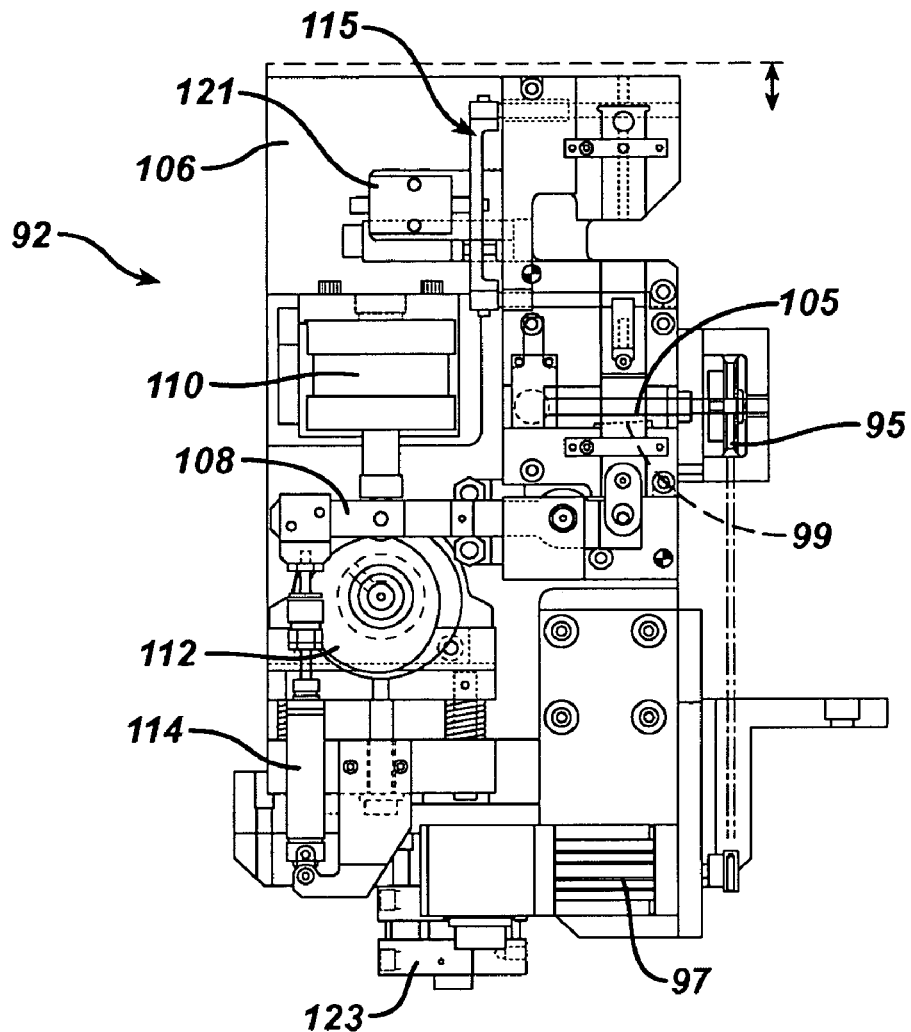
FIG. 12 is a front view of a swage assembly of the system shown in FIGS. 1–11.
Figure 13:
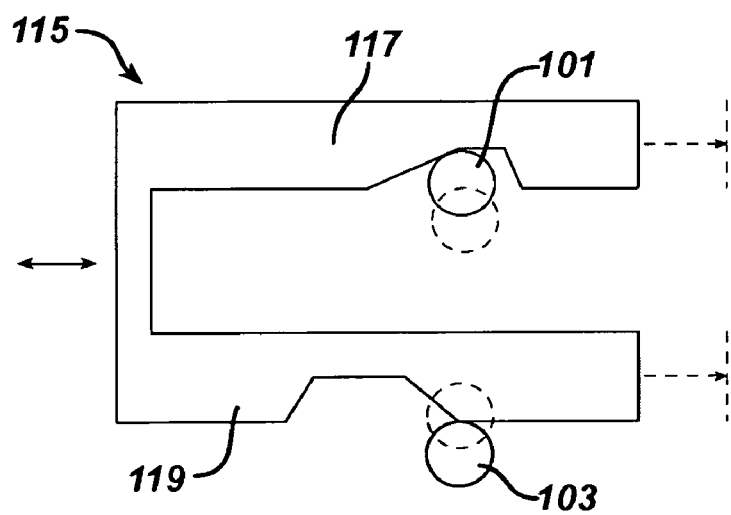
FIG. 13 is a diagram of a funnel position control mechanism of the system of FIGS. 1–12.
Figure 14:
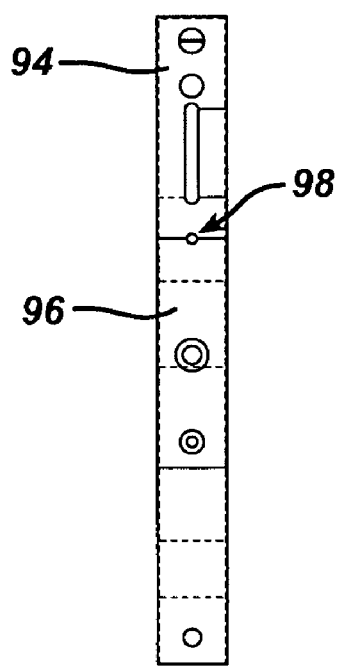
FIGS. 14, 15 and 15A are front, side and enlarged views, respectively, of swage dies and suture funnels in accordance with the present invention.

As shown in FIGS. 1, 9–11 and 22, the system 10 has a precisor 78 to establish a specific orientation and insertion depth for a needle 3 that is inserted into the precisor 78 (in preparation for insertion into the swaging station 92). The needle 3 is shown in FIG. 11 in two positions, viz., pointed up (solid lines) and pointed down (dotted lines). The precisor 78 has a pair of opposed, pneumatically-controlled needle gripping fingers 80a, 80b which receive and hold a needle 3 passed thereto by gripper unit 56c (which received the needle 3 from the in-feed robot 34). The optical sensors 28, 30 can discern the blunt end 5 of the needle 3, which has the suture hole 4, from the pointed end 6. Based on this data, the robot 34 hands the needle 3 to the gripper 56c in a position for inserting the blunt end 5 between the precisor needle gripping fingers 80a, 80b. Once positioned within the precisor needle gripping fingers 80a, 80b, the depth of insertion of the blunt end 5 of the needle 3 can be adjusted by bumping the blunt end 5 with a push block 82 which is urged forward and backward under the control of a solenoid or pneumatic cylinder 84. The projection of the push block 82 in a forward direction can be precisely controlled by a micrometer adjuster 86. The precisor 78 may be provided with a rotatable mount 88 which is rotatable relative to the base 79 under pneumatic or electronic control to position the needle 3 such that it is curved in the preferred direction: up, down, right or left. As noted above, with reference to FIG. 11, a needle 3 which is inserted into the gripper fingers 80a and 80b by the blunt end 5 could be curved up or down, as shown. Cameras 28 and 30 are utilized to discern the direction of curvature of the needle 3 and inform the system controller 32 to rotate the rotatable mount 88 in the proper direction in order to position the needle 3 for transfer to the swaging station 92, i.e., via needle gripper unit 56b.

As shown in FIGS. 12 through 15A, the swaging station 92 has a pair of opposed dies 94, 96 which, when positioned in close adjacency, define a swage opening 98. The swage opening 98, as is conventional for swaging dies made for this purpose, is smaller in at least one area along its internal circumference than the outer circumference of the blunt end 5 of a needle 3 prior to swaging. For example, the swage opening 98 may approximate a square in shape having a side length less than the outer circumference of the needle 3. Prior to insertion of a needle 3 into the swaging station 92, the swaging dies 94, 96 are opened such that a needle 3 may be received in the swage opening 98 loosely. The opposing swaging dies 94, 96 are brought into closer and closer proximity until they are actually in contact with the outer surface of the needle 3 sufficient to grip the needle 3. As can be appreciated from FIG. 15A, there is not much room for error as regards the insertion depth of the needle 3 into the swage opening 98. The precisor 78 provides the necessary degree of precision. After the suture 7 has been inserted into the needle 3, the swaging dies 94, 96 are forcefully brought closer together and the blunt end 5 of the needle 3 is crimped to collapse the suture hole 4 and retain the suture 7 therein. The apparatus for performing swaging is described further below.

Figure 15:
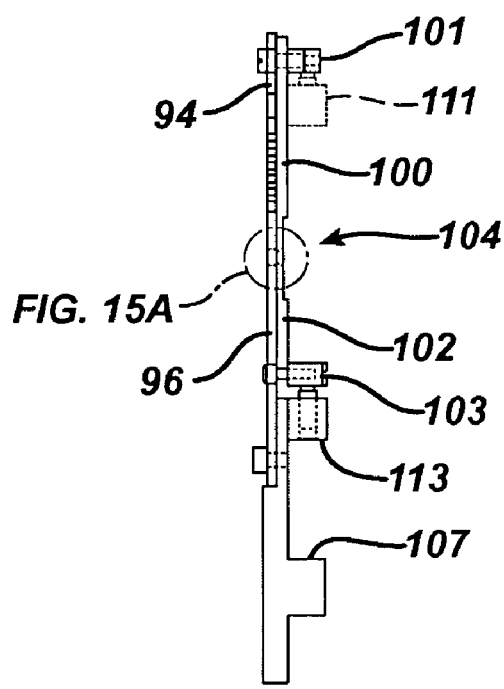
Figure 15A:
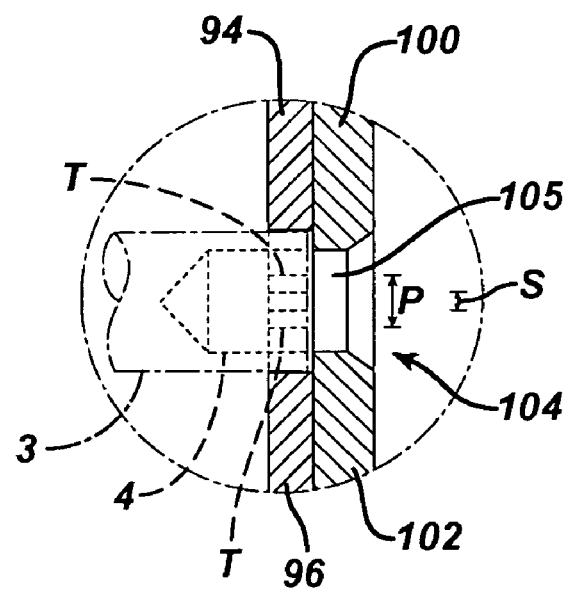

As shown in FIG. 15, the insertion of suture 7 into the suture hole 4 formed in a needle 3 is facilitated by a pair of funnel portions 100, 102 which are held in the swaging station 92 proximate to the swage dies 94, 96 to aid in guiding the end of the suture 7 into the suture hole 4. When held together in abutment, the funnel portions 100 and 102 define a suture opening 104 which converges from a relatively large size to the size of the suture hole 4 in the needle 3. The converging opening 104 shown in FIG. 15A is enlarged for purposes of illustration. The outlet end 105 of the converging opening 104 is approximately the size of the suture hole 4. The converging opening 104 is positioned coaxially with the suture hole 4 to aid in inserting an end of a suture 7 into the suture hole 4 of a needle 3 held in swage dies 94, 96. FIG. 15A shows a needle 3 held in swage dies 94, 96 which are in preclamp position. In preclamp position, the terminal ends T of the dies 94, 96 are separated by a distance "P". When swaging occurs, the ends T of dies 94, 96 converge to a spacing "S". The dies 94, 96 are prevented from coming into direct abutment, even during swaging by a tapered stop block 105 against which a die block 107 impinges during swaging. The position of the stop block, i.e., its left-to-right position, is controlled by a pulley 95 turned by a chain or belt by drive motor 97. Turning the pulley causes an internal shaft coupled thereto to threadedly engage the stop block 105, moving to the right or left and displacing the stop ramp 99 to adjust the height attainable by the die block 107 and associated swage die 96. The opened and closed position of the swage dies 94, 96 within the swage framework 106 is controlled by the swage lever 108 pivoting upon pin 109 and having, one end which acts upon swage die 96 and another end which is moved by swage cylinder 110 preclamp cam 112 and clamp cylinder 114. The clamp cylinder 114 pulls the swage lever 108 down under spring tension (the spring is housed in the clamp cylinder 114). The preclamp cam 112 acts upon the swage lever 108 to allow the clamp cylinder 114 to pull the swage lever 108 at a controlled rate, preventing inadvertent swaging of the needle that would otherwise occur due to a rapid acceleration of the swage lever 108 by the unconstrained action of the clamp cylinder 114. The preclamp cam 112 allows the clamp cylinder 114 to pull the swage lever 108 down to position the swage dies 96 and 94 close enough together to exert sufficient force upon a needle 3 inserted therein to retain the needle 3 there-between. In the embodiment shown in FIG. 12 the upper swage die 94 is stationary and the lower swage die 96 moves under the control of the swage lever 108 to swage the needle 3. Note that the swage dies 94, 96 are not installed in the swage framework 106 in FIG. 12. After the suture 7 has been inserted into the needle hole 4, the preclamp cam 112 is rotated to a position wherein the needle 3 is clamped and permitting the actuation of the swage cylinder 110 which forcefully depresses the swage lever 108, thereby urging the swage dies upward until it is stopped by the stop block 105, resulting in the swaging of the end 5 of the needle 3 and clamping the suture 7 in the needle hole 4. This basic swaging apparatus and methodology is known and shown in the above described U.S. Pat. No. 6,263,558. The adjustable stop block 105 allows the swage die opening to be adjusted based upon feedback from pull testing of the suture attachment strength (to the needle 3).

Unlike previously known swaging apparatus, the funnel portions 100, 102 are opened after insertion of the suture 7 into the suture hole 4 and prior to swaging. This step prevents the funnel portions 100, 102 from contacting and damaging the suture during and after the swaging operation. In reference to FIGS. 13 and 15, the funnel portions 100, 102 each have positioning pins 101, 103, respectively, which control the opening/closing of the funnel portions 100,102. More particularly, each pin 101, 103 is urged upwardly by a ball and spring assembly 111, 113. The pins 101, 103 extend through the swage dies 94, 96 and are free to move through the necessary motion path due to enlarged openings in the swage dies 94, 96. As a result, the funnel portions 100, 102 may be moved independently of the swage dies 94, 96. Ball and spring assembly 113 urges funnel portion 102 upwardly, which is the closed position for that portion. Ball and spring assembly 111 urges funnel portion 100 upwardly, which is the open position for that funnel portion. A control yoke 115 has first and second cam rods 117, 119 which extend into the swage framework 106 and bear upon the pins 101, 103. When the yoke 115 is in the leftward position shown, pin 101 is free to rise under the influence of ball and spring assembly 111 and pin 103 is pressed down against ball and spring assembly 113, resulting in the funnel portions 100, 102 being open. If the yoke 115 is pushed to the right, i.e., by a pneumatic control cylinder 121, the pins 101, 103 assume the positions indicated in dotted lines and the funnel portions 100, 102 are closed. The foregoing features allow the funnels to be closed prior to and during suture insertion in a suture hole 4 of a needle 3 clamped between the swage dies 94, 96, then opened prior to swaging. In this manner, the funnel portions do not contact the suture 7 during or after swaging and therefore avoid distorting or cutting the suture 7.

Another attribute of the swaging station 92 of the present invention is that the entire swage framework 106 may be raised and lowered on a track or keyway by a lift cylinder 123. The purpose of this feature is to move the upper, stationary swage die 94 out of the path of a swaged needle 3 of an armed suture 2 which is moved horizontally from the swage station 92 by needle gripper unit 56a to the pull test station 126.

Figure 16:
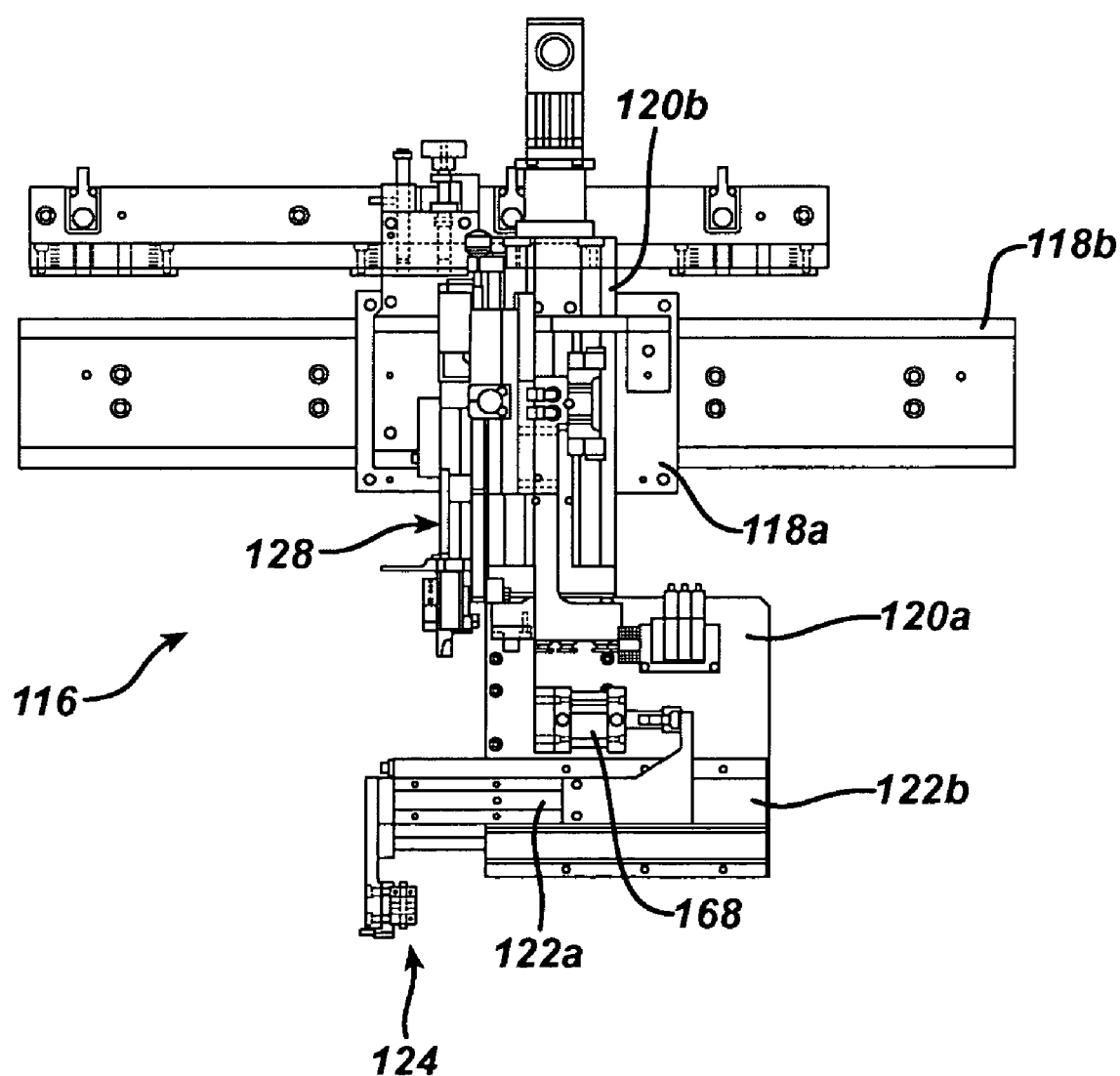
FIGS. 16–18 are plan, front and side views, respectively, of a suture transfer gripper and suture cutter assembly of the system shown in FIGS. 1–15.
Figure 17:
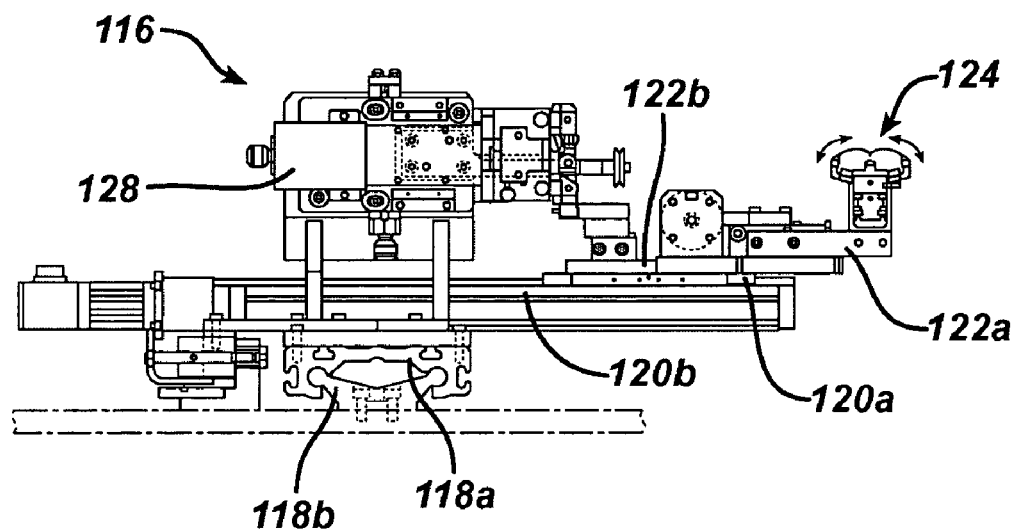
Figure 18:
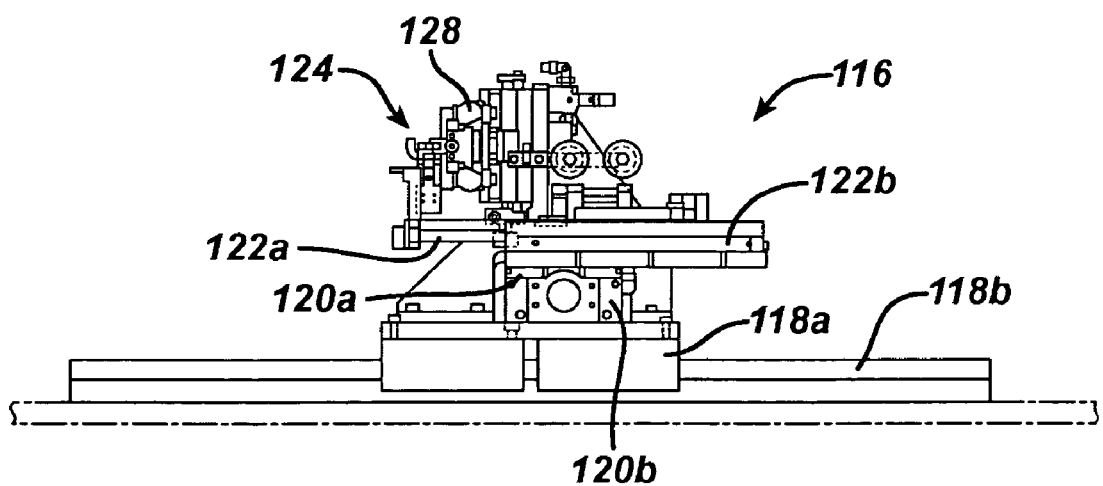

FIGS. 16–18 show stacked slide assembly 116, which includes a first slide table 118a sliding upon a mating track 118b. The first slide table 118a supports a second slide table 120a, sliding upon a linear slide 120b (driven by a screw drive or linear motor which defines a second mating track element for second slide table 120a and which is disposed perpendicular to track 118b. The second slide table 120a supports a third slide table 122a which slides on mating track 122b perpendicularly to linear slide 120b and parallel to track 118b. The third slide table 122a supports the suture transfer gripper 124. The compound construction of the stacked slide assembly 116 permits the suture transfer gripper 124 to execute motions parallel and perpendicular to the linear motor 64 and parallel and perpendicular to the suture 7. This range of motions enables the suture transfer gripper 124 (which is disposed on the highest tier in the stack) in cooperation with suture grippers 70, 72 to maintain control of the suture 7 before, during and after the processes of cutting, inserting the cut end of the suture into the needle 3 as well as, during the transfer of the swage needle/suture combination (the armed suture 2) to the pull test station 126.

The suture 7 is protected from damage throughout its processing by the system 10, which is important to guarantee quality control. This is accomplished for example, when the transfer gripper 124 grasps the suture 7 at the cut end and transfers it to the pull test station in synchronism with needle gripper unit 56a at the needle end, as shall be explained further below. The first slide table 118 also supports the cutter assembly 128 that is employed to cut the suture 7 to the prescribed length required for a specific application. The upper slide table 122a moves the suture transfer gripper 124 to positions in front of and to the rear of the cutter mechanism 128. The middle, second slide table 120a moves the suture transfer gripper 124 and any suture 7 held therein from right to left between alignment with the swage station 92 and alignment with the pull test station 126. The bottom slide table 118a allows the entire assembly 116 to be manually adjusted so that the cutter assembly 128 can cut different length sutures. The suture transfer gripper 124 serves a dual purpose in that it is used for maintaining control of the end of suture 7 during the suture insertion process, as well as during the suture transfer process (to the pull test station). The bottom slide table 118a has sufficient travel to allow for different length sutures, e.g., 18-inch through 36-inch long sutures. The suture transfer gripper 124 may be positioned either ahead of or behind the suture cutter 128 and extends upward toward the suture 7 from its mounting on the third slide table 122a. In contrast, the suture insertion gripper 70 extends downward toward the suture 7 from the suture tower assembly 66. Both the suture transfer gripper 124 and the suture insertion gripper 70 may be operated along a line parallel to the suture 7 as it runs from the payout spool 148 to the swaging station 92. The suture transfer gripper 124 and the suture insertion gripper 70 pass one another along this parallel line of travel when one or both are in the open position. In this manner, a "hand-over-hand" type of motion can be executed by the suture transfer gripper 124 and the suture insertion gripper 70 as the suture 7 is advanced toward the swaging station 92 and is processed by cutting, etc.

During single needle mode, as well as during preparation for insertion of suture 7 into the first needle 3a of double-armed sutures 2, the suture transfer gripper 124 will be positioned ahead of the cut point of the cutter assembly 128 just prior to and during cutting. As shall be explained further below, while cutting for the second needle 3b of a double-armed suture 2, the suture transfer gripper 124 will be behind the cut point while the inverted insertion gripper 70 (pointed toward the suture payout spool 148) is holding the suture approximately 3/16 of an inch above the cut point. Following the cut, the suture tower 66 rotates the insertion gripper 70 (and the suture 7 gripped therein) 180° and inserts the end of the suture into a waiting (second) needle 3b held in the swage assembly 92. The suture transfer gripper 124 then moves to a position ahead of the cut point and waits for the suture insertion gripper 70 to rotate back to a front-facing orientation and position itself approximately ³⁄₁₆ of an inch behind the cut point. This will produce a small suture remnant every other cycle while in double needle mode.

Figure 19:
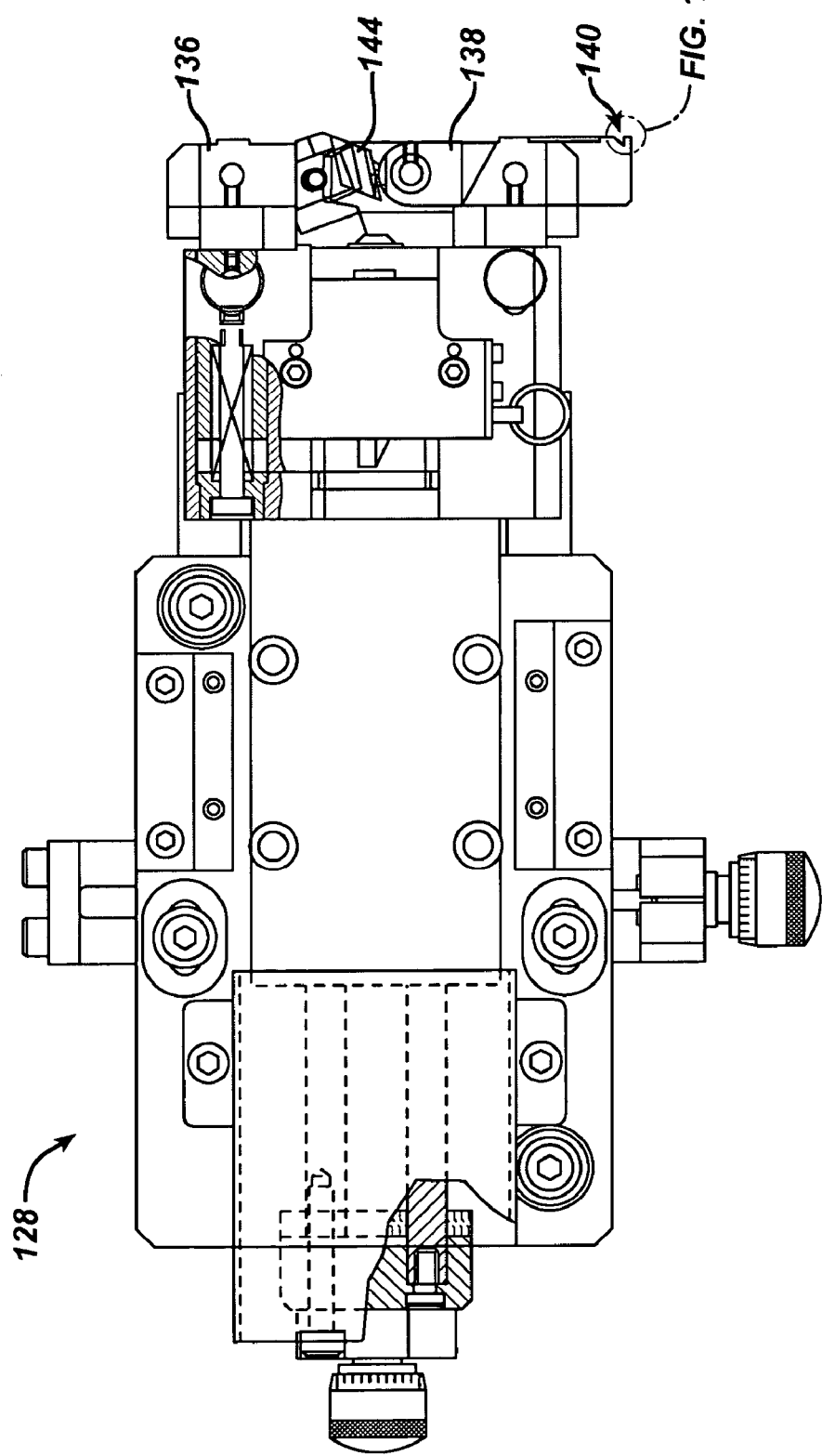
Figure 20:
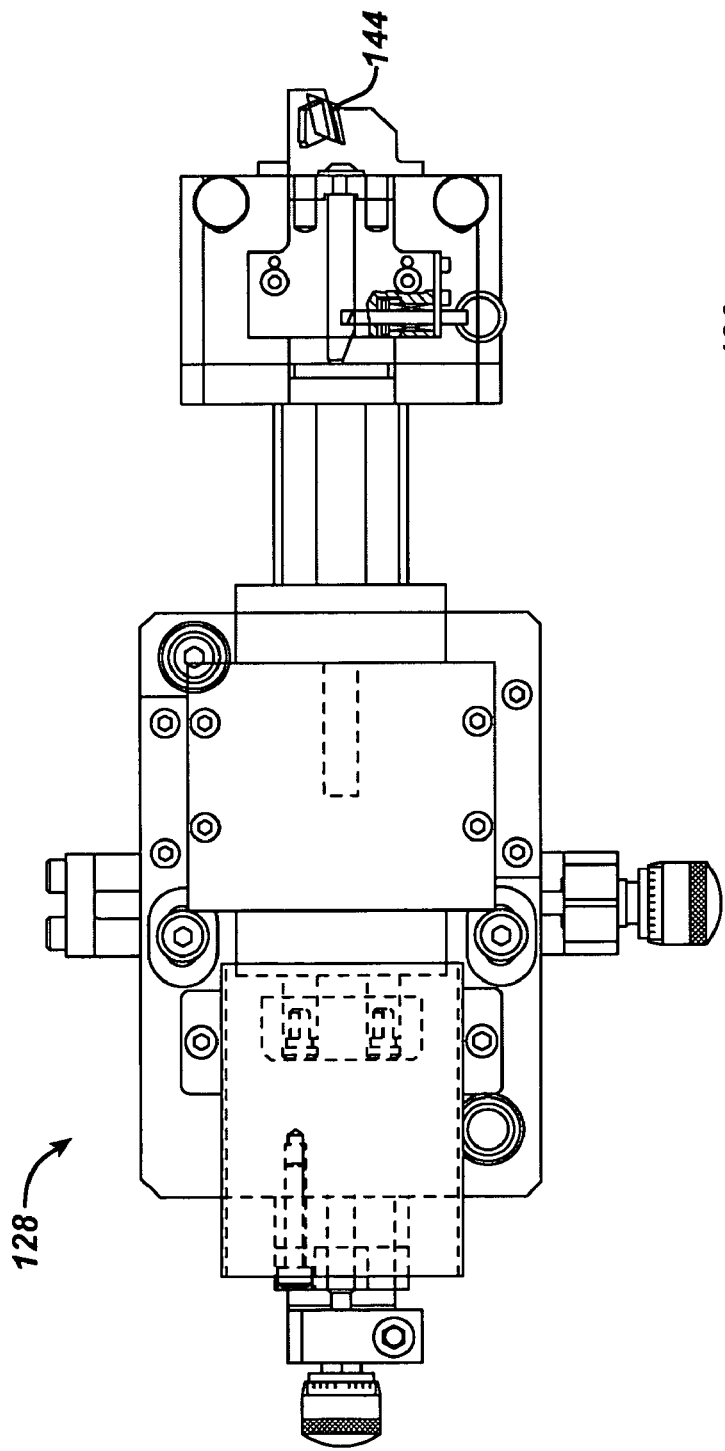
Figure 20A:
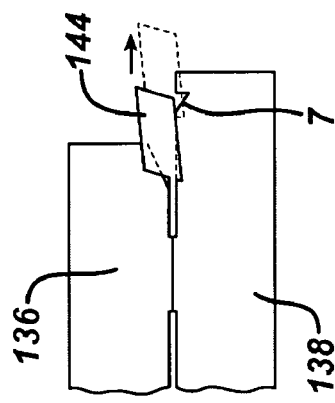
Figure 21:
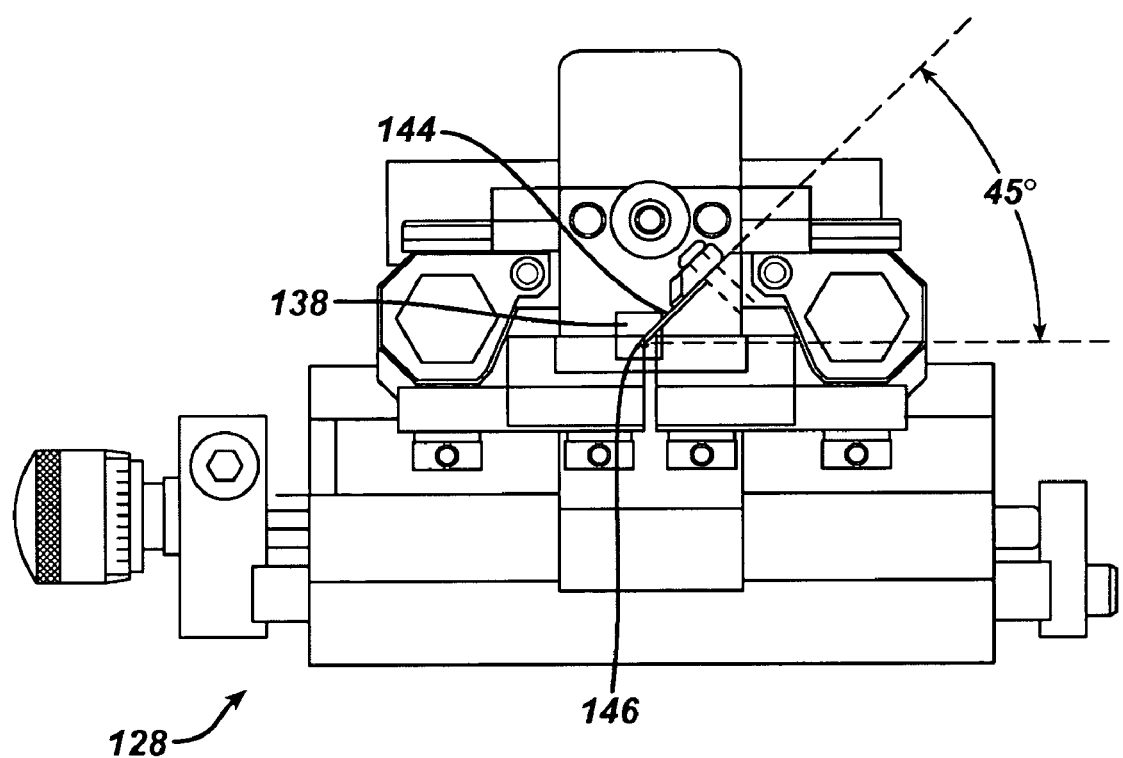
FIG. 21 is a front view of the suture cutter of FIGS. 19 and 20.

As shown in FIGS. 19 through 21, the cutter assembly 128 of the present invention has features in common with, as well as additional features and modifications over the cutter shown in U.S. Pat. Nos. 6,058,821 and 6,263,558. These common and new features aid in the execution of the fabrication of single and double-armed sutures 2 by the present invention, in particular, as applied to the fabrication of very fine gauge sutures 2 using monofilament suture material. As shown in FIG. 19A, cutter assembly 128 has suture control arms 136 and 138 which deploy by pivoting toward each other when the cutter 128 is extended. Simultaneously, a cutter blade 144 projects forward to cut the suture 7. The suture control arms 136, 138 have been modified in the present invention, namely, control arm 136 has been truncated and the suture notch 140 in control arm 138 has been modified by rotating the outer suture support surface 142 of the notch 140 so that it is perpendicular to the direction of cutter travel when the suture support arm 138 is deployed to support the suture 7 for cutting. In this manner, a single suture control arm, namely suture control arm 138, is sufficient to support the suture 7 during the cutting operation, in that the suture 7 is trapped between the cutting blade 144 and the suture support surface 142, which is disposed at about 90 degrees relative to the advancement direction of the cutting blade 144. As a result, the first suture control arm 136 need not have a complimentary suture grasping notch for capturing the suture, and may be truncated at the end to allow greater freedom in the orientation of the cutting blade 144 which has also been modified. More particularly, the cutting blade is now held at an angle relative to the vertical, e.g., 45 degrees. This is shown in FIG. 21. The angle of the cutting blade 144 results in a suture 7 which has a cut end with a taper. This taper provides a pointed end on the suture 7 which is smaller in cross-sectional area than the cross-sectional area of the suture distal to the taper, e.g., as would be presented if the suture were to be cut at a 90 degree angle. By reducing the cross-sectional area of the suture end, the task of aligning the cross-sectional area of the suture 7 with the suture hole 4 in the needle 3 is less critical, facilitating suture insertion despite some degree of misalignment between the suture 7 and the suture hole 4. A tapered point on the suture end that is inserted into the suture hole 4 also increases the flexibility of the end of the suture 7, such that the suture can bend and find its way into the suture hole 4 more readily than if the suture had a blunt end. As noted above, the truncated end of suture control arm 136 permits the cutter blade 144 to be positioned at an angle. The second suture control arm 138 is also modified to accommodate the angled suture cutter, namely, an angled slot 146 is provided in the end thereof (see FIG. 21) which accommodates the cutter 144 when it extends through suture control arm 138 to cut the suture 7 during the cutting stroke.

Figure 22:
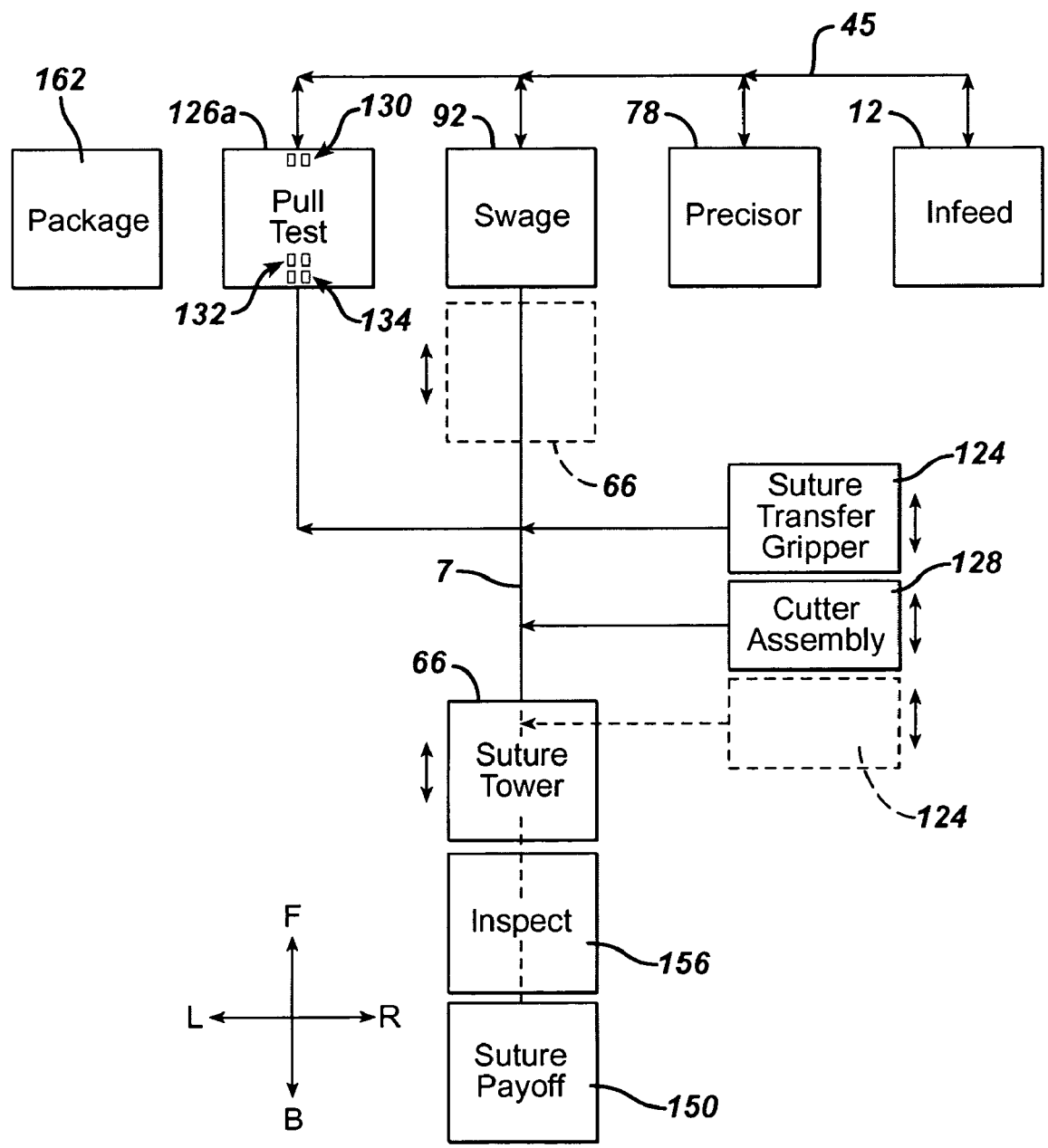
FIG. 22 is a schematic diagram showing the system of FIGS. 1–21.

FIG. 22 diagrammatically shows the overall layout and movement of materials within the system 10. In referring to the direction of movement and/or position of elements, the convention established by the four direction indicator, wherein "F" stands for front, "B" for back, "R" for right and "L" for left shall be used. The system 10 is generally T-shaped with the in-feed 12, precisor 78, swage 92, pull test 126 and packaging 162 stations arrayed across the front of the system 10 in a line substantially equally spaced apart. At the very front of the system 10, the needle transfer system, i.e. the needle transfer assembly 45 (shown diagrammatically) sequentially transfers needles 3 as they are processed by each of the processing stations in a right to left direction with the three gripper units 56a–c moving in and out toward the processing stations 12, 78, 92, 126. The suture movement is in the back to front direction, namely, from a suture pay-off station 150, which contains a spool 148 of suture material (see FIG. 2) through an inspection station 156 and up to the swage station 92. The suture payoff assembly 150 is utilized in conjunction with the suture tower assembly 66 to supply suture 7 from a suture spool 148 at a linear speed synchronized with the indexing of the suture tower assembly 66. The suture payout assembly 150 includes a motor which rotates the suture spool 148 at a rate relative to suture pulling by the suture insertion gripper 70. The suture insertion gripper 70 provides a pre-selected tension in the suture 7. Spring-loaded and/or weighted bobbins 152 aid in maintaining a suitable tension in the suture 7, as well as providing a means to absorb variations in suture payout rate. The inspection system 156 for finding suture defects is installed between the suture payoff assembly 150 and the suture tower assembly 66. Conventional mechanical defect sensors may be employed or optical (laser-based) sensors may be used to sense on suture defects. Co-pending Application No. (to be assigned), entitled "Improved System and Method for Sensing Variations in a Strand", filed on Oct. 10, 2003 and owned by the Assignee of the present application discloses a suitable suture defect detector for use with fine gauge sutures and is incorporated herein by reference. Signals informing of any defects are sent to the controller 32, which then directs the remainder of the system 10 in a manner which halts further processing until the length of suture containing the defect is purged from the system. Defects are removed by pulling and cutting sufficient lengths of suture 7 (without swaging) to assure that the defect has been discarded. All discarded suture material is automatically vacuumed from the system via a vacuum system 158 with ports 160 disposed below the system 10 at locations where waste is likely to be generated. During this suture defect culling routine, the needle 3a or 3b waiting to be swaged is held in a retracted position so that a suture will not be inserted into it. This prevents sutures with defects from unintentionally being caught and swaged into a needle. The suture 7 is pulled from the spool 148 and the free end thereof is delivered to a needle held in the swage station by the suture tower 66 which moves along the linear motor 64 parallel to the suture 7 between the inspection station and the swaging station 92. A suture cutter is disposed to the right of the suture line but projects to the left for cutting the suture into appropriate lengths as determined by the application for which the suture is ultimately used. The suture transfer gripper 124 is disposed below the suture 7 line and can be extended leftwardly such that a suture gripped at the end by the suture transfer gripper 124 and at the needle end by a needle gripper unit 56a that can be moved to the left under tension to the pull test assembly 126. A tension release cylinder 168 is utilized to allow a length of suture 7 stretched between the suture transfer gripper 124 and needle gripper unit 56a to assume a relaxed, unstretched state before the transfer gripper 124 is opened. If the suture transfer gripper 124 were opened when the suture 7 were under tension, the end released would spring forward under the impetus of the elastic return of the suture to a relaxed state. By releasing the tension in the suture 7 under the control of the tension release cylinder 168, unwanted suture motion can be avoided. The pull test station 126 receives the needle 3 portion of an armed suture 2 in a first gripper 130 and the suture, in a suture gripper (either 132 or 134). The needle gripper 130 and the suture gripper 132 or 134 are then urged apart, creating a controlled tension to test the strength of affixation of the suture 7 to the needle 3. It is preferred that the present system 10 utilize non-destructive testing for every armed suture 2 produced, such that each suture 2 is verified to have sufficient strength of connection between the needle 3 and the suture 7. In addition, the present system 10 utilizes periodic destructive testing wherein a sample, e.g., one of every fifty sutures produced, is subjected to increasing tension until the suture 2 breaks. In this manner, data can be collected reflecting average maximum strength and whether breakage is attributable to the suture itself or to the suture/needle junction. In addition, this data can be used to adjust the swaging stop block 105. Pull test mechanisms are known, such as those mechanisms and related processes disclosed in U.S. Pat. Nos. 5,487,308, 5,793,634, 5,844,142 and 5,918,284, each owned by the assignee hereof and incorporated by reference herein. Due to the generally horizontal orientation of suture in the present invention, it would be necessary to orient the pull test mechanism 126 in a generally horizontal direction. For example, the pull test assembly of FIGS. 20–21*b* of U.S. Pat. No. 5,844,142 is shown with a vertical orientation. This assembly could be reorientented horizontally to operate with the present invention (the suture grippers 425*a*, 425*b* opening to the right in the present invention 10, to receive a suture stretched between the suture transfer gripper 124 and an attached needle held by needle gripper unit 56*a*). To reorient the pull test apparatus of U.S. Pat. No. 5,844,142 horizontally, the counterweight 476 thereof would also be required to be suspended downwardly (at 90 degrees to the orientation shown in the U.S. Pat. No. 5,844,142). The pull test assembly 126 preferably has three grippers, viz., a needle gripper 130, a first suture gripper 132 with a pair of rubber-padded gripper fingers 132*a*, 132*b*, used for minimum pull testing and a second suture gripper 134 with a pair of serrated gripper fingers 134*a*, 134*b* used for destructive pull testing. Depending upon the cycle's requirement, either the first (minimum) or the second (destructive) gripper 132,134 will be activated, i.e., by spring tension or pneumatically as described in U.S. Pat. No. 5,844,142. It should be noted that the needle gripping "V" plate supporting arm 436 of the U.S. Pat. No. 5,844,142 may be replaced with a pneumatic gripper 130 as described herein.

Having passed the pull testing, the armed suture 2 is then transferred to the left by the out-feed robot 35 for packaging by the package station 162. The out-feed robot 35 is of the same type as the in-feed robot 34 and is used to remove armed sutures 2 from the pull test station 126 and insert them into a package 170 (see FIG. 2). Packages 170 will be presented to a needle loading area 171 via a conventional package slice feed mechanism 162 (gravity fed escapement). The out-feed robot 35 and the package slice feed mechanism 162 are programmatically coordinated. Once a package 170 has been loaded with an armed suture 2, there are a number of conventional means and methods for transporting the package 170 away from the system 10 for further processing, leading to shipment to the ultimate user. In the embodiment shown in FIG. 2, a pick and place apparatus 180 with a slide 182 on which a gripper arm 184 articulates is used to remove the filled package 170 from the package transfer slide 172. The gripper arm 184 carries an extensible gripper that extends down, grasps the package 170, and pulls the package off the package transfer slide 172. The package 170 is then moved with the gripper arm 184 on the slide 182 until the package 170 is positioned above an off-load conveyor 186 whereupon the package 170 is released by the gripper and falls on the off-load conveyor 186. The off-load conveyor 186 carries the loaded package 170 to an operator 188 who places the package 170 on a winder table 190 in order to wind the suture 7 into the package 170 for further processing.

Figure 23:
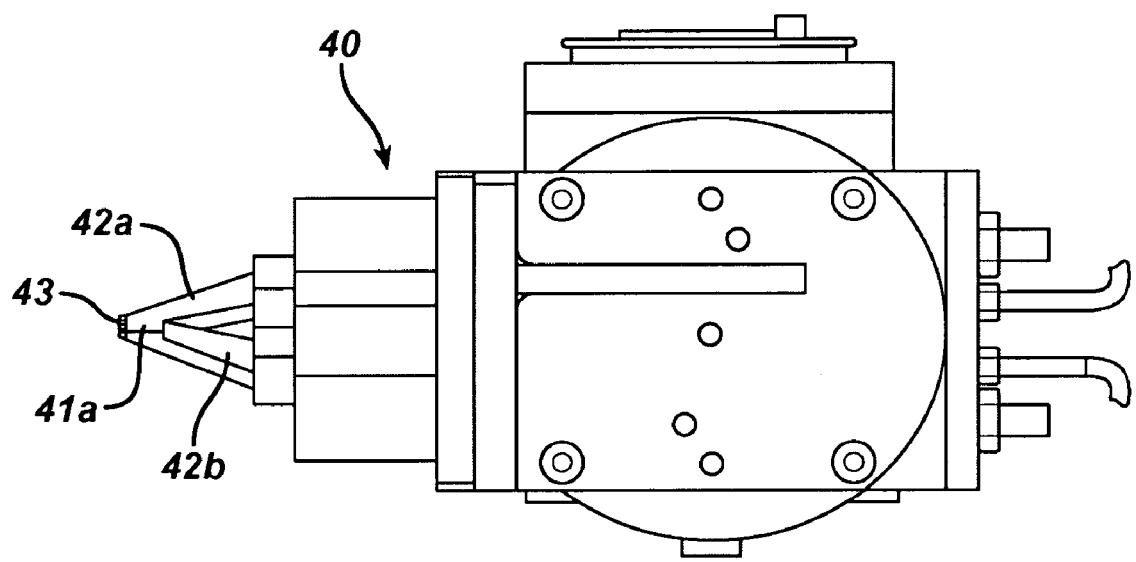
FIG. 23 is a plan view of a robotic needle gripper.
Figure 24:
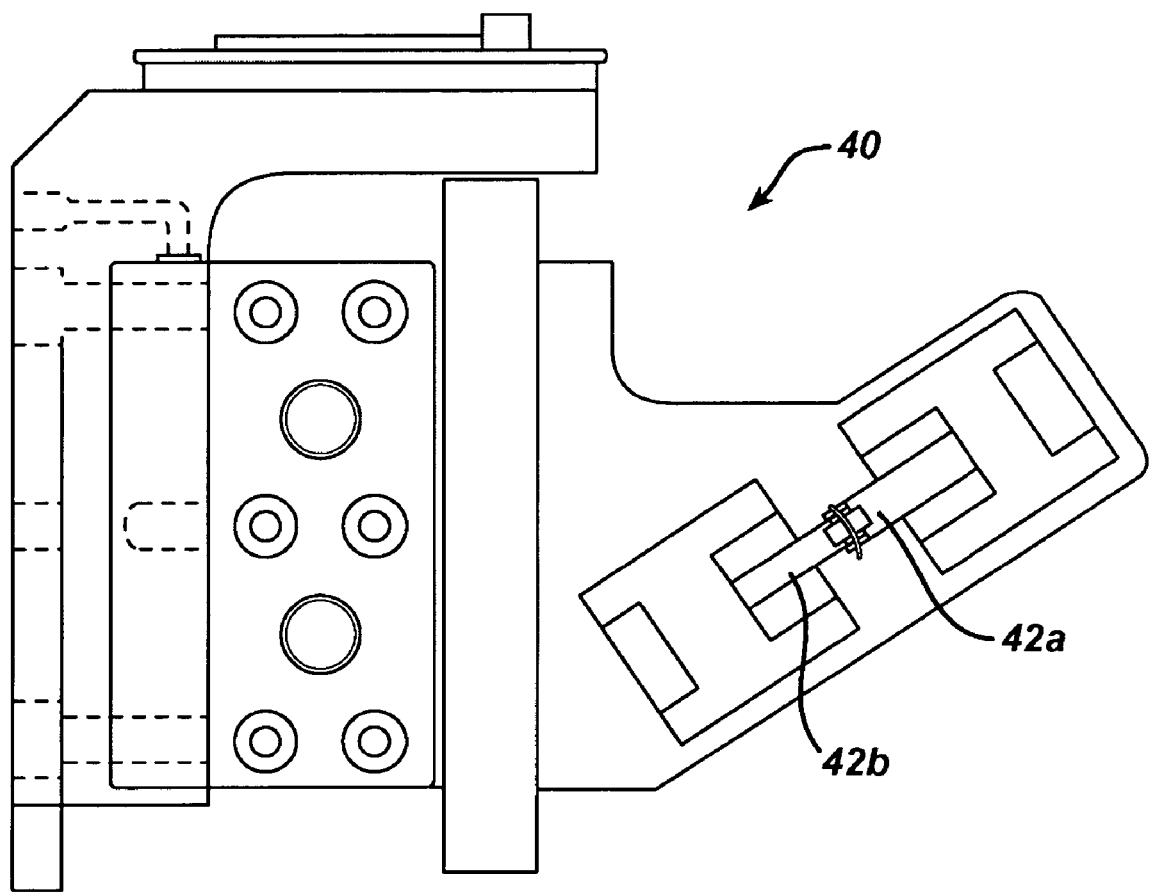
FIG. 24 is a front view of the robotic needle gripper of FIG. 23.
Figure 25:
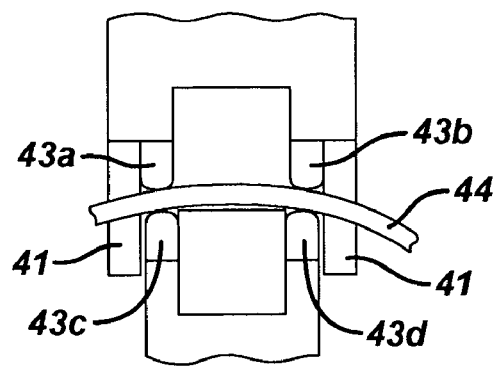
FIGS. 25 and 26 are enlarged views of needles with different radii of curvature held in the robotic needle gripper of FIGS. 23 and 24.
Figure 26:
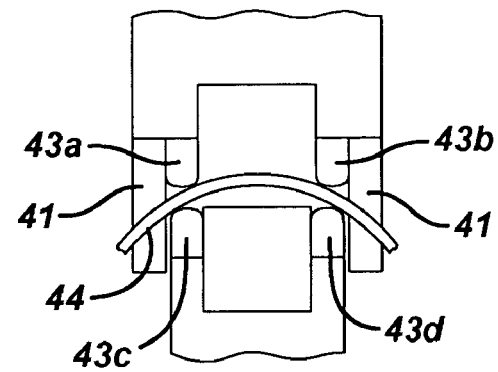

FIG. 23 shows a robotic end effector 30 that may be advantageously used on the in-feed and out-feed robots 34, 35 which has unique, overlapping needle gripper fingers 42*a*, 42*b*. More particularly, finger 42*a* has a pair of needle abutments 41*a*, 41*b* that depend from finger 42*a* and embrace finger 42*b*, which inserts therebetween. As shown more clearly in FIGS. 25 and 26, each needle gripping finger 42*a*, 42*b*, has a pair of radiused gripper pads 43*a*, 43*b* and 43*c*, 43*d*, respectively. Each of the radiused gripper pads 43*a–d* contact a needle 3 gripped therein at a single point. Since the gripper pads are radiused, they can grip needles having different radiuses, as shown by comparing FIGS. 25 and 26. More particularly, different sets of points on the gripper pads 43*a–d* contact the differently radiused needles 3 of FIGS. 25 and 26. The curvature of the needle 3 grasped by the needle gripper fingers is established by the fact that the needles are lying on a flat surface, viz., in-feed conveyors 20 and 22. The gripper fingers 42 come down upon a needle 3 lying on the conveyor, e.g., 20 with the gripper fingers 42 open sufficiently to accommodate the needle 3 therebetween. When the needle gripper fingers 42 are fully down on the needle 3 to be picked up, the needle abutments 41*a*, 41*b* contact the needle to maintain it in an orientation where the curvature of the needle is a plane parallel to the abutments while the gripper fingers 42 are closed and the needle is captured between the opposing pairs of gripper pads, viz., 43*a*, 43*b* and 43*c*, 43*d*. Having described the apparatus of the system 10, the operation thereof will be described below. In this regard, it should be noted that the system 10 has four operating modes, viz, Setup, Single cycle, Initialization and Run Mode.

In run mode, the system 10 cycles continuously during the production of single or double-armed sutures 2. In single cycle mode, single steps (sequential states) of system 10 are initiated using a pushbutton on the operator console or via an operator pendant. In setup mode, the operator has the ability to operate individual actuators or assemblies as well as be able to "jog" selected servo motors. Initialization mode is used to initialize the system 10 (place all components in a predefined starting position on state) on startup, after a power down or fatal alarm occurrence. A description of the operation of the various subassemblies of the system 10 in the Setup, Initialization and Run modes is set forth below.

Setup Mode

When the system 10 is placed in setup mode, individual components of the system 10 may be selected via an operator interface to the controller 32 for operational control. When in Setup, the following capabilities will be accessible to maintenance personnel relative to the needle transfer assembly 45: toggle, single cycle or continuous cycle each of the three gripper units 56*a–c* in/out actuators and each of the three individual needle gripper finger pairs 58*a–c*; home the needle transfer assembly 45; jog the needle transfer assembly 45 forward and backward in increments of 0.001", 0.010" and 0.100"; home the suture transfer gripper 124; jog the suture transfer gripper 124 forward and backward in increments of 0.001", 0.010" and 0.100"; and single cycle both the needle transfer assembly 45 and the suture transfer gripper 124.

When the needle precisor 78 is selected in setup mode, the following capabilities will be accessible to maintenance personnel: to toggle, single cycle or continuous cycle the needle gripping fingers 80a, 80b, the push block 82, and the rotatable mount 88. In setup mode, the swaging assembly 92 is capable of the following actions: toggle, single cycle or continuous cycle the suture funnel control cylinder 121, the pre-clamp cam 112, the swage cylinder 110, the swage assembly lift cylinder 123; home the swage die adjustment servo 97; move the swage die adjustment servo 97 to it's initial working position; jog the swage die adjustment servo 97 in and out in increments of 0.001", 0.010" and 0.100"; single cycle the entire assembly 92 in combination with the suture tower assembly 66; and single step the entire assembly 92 in combination with the suture tower assembly 66.

In setup mode, the suture tower assembly 66 exhibits the following capabilities: toggle, single cycle or continuous cycle the suture cutter 128, the suture transfer gripper 124, the suture transfer gripper slide table 122a, the suture tensioning cylinder 168, the suture insertion gripper 70, and the suture insertion gripper turret 68; home the suture tower assembly 66; move the suture tower assembly 66 to its working positions for the selected suture length; jog the suture tower assembly 66 in increments of 0.001", 0.010" and 0.100"; and single cycle the suture tower assembly 66 in combination with the swage assembly 92. In setup mode, the pull test assembly 126 executes the following: to toggle, single cycle or continuous cycle the minimum pull test grippers 132 and the needle hold grippers 130; single cycle and single step all the grippers 130, 132, 134 through a normal sequence. The needle parking/package feeder assembly 162 can: toggle, single cycle or continuous cycle the slice feed actuator 163, the package insertion actuator 173 and the package transfer slide 172 in Setup Mode. For all the foregoing actions in Setup Mode, timers are provided to monitor end point actuation.

Initialization

During initialization, the following actions are performed by the needle transfer assembly 45, in sequence. The three needle gripper units 56a–c will open. The in/out pneumatic actuators of gripper units 56a and 56b will retract and gripper unit 56c will extend. The linear actuator 47 will execute a homing routine whereby the needle transfer assembly 45 is positioned closest to the in-feed station 12. The three needle gripper units 56a–c close. During initialization, precisor 78 does the following in sequence. The needle gripping fingers 80a, 80b are opened, the push block 82 is retracted and the rotatable mount 88 rotates to its home position. At the swage station 92, the suture funnel portions 100, 102 open. The swage cylinder 110 and the needle clamp cylinder 114 retract. The preclamp cam 112 is rotated to maximum interference with the die actuation arm 108 and the swaging assembly offset cylinder 123 raises the entire swage assembly 92 to its "clear" position. The swage die adjustment servo 97 then performs its homing routine.

Prior to initialization, the operator manually feeds a suture 7 from the suture payoff assembly 150 through the inspection system 156, past the cutter assembly 128 to the swaging assembly 92, where it is tied off. The following actions are then performed in sequence. A suture length sensor will be checked to insure that the cutter assembly 128 is set to the desired suture length. The suture cutter 128 then retracts. The turret 68 of the suture tower assembly 66 rotates to its home position and the suture transfer gripper 124 and suture insertion gripper 70 open. The suture tension release cylinder 168 retracts. The linear motor 64 performs a homing routine, with the suture tower assembly 66 moving the suture insertion gripper 70 to a position behind the cutter 128. The suture insert gripper 70 then closes on the suture 7 and the suture cutter 128 cycles to the cutting position and back to the retracted position (close and open) to cut the suture. At the end of initialization, the operator removes the initial scrap length of suture attached to the swaging assembly 92 prior to invoking run mode. During initialization, all grippers 130,132 and 134 at the pull test station 126 are opened.

During initialization, the out-feed robot 35 waits for the "System Running" signal.

The needle gripper fingers 42 then open and the robot 35 moves to its needle pick up position at the pull test assembly 126. The needle gripper fingers 42 close and the robot 35 asserts its "ready" signal to the system controller 32. The package slice feed actuator 163, which moves packages 170 horizontally, retracts to its home position (out). The package inserter actuator 173, which moves the packages 170 vertically, retracts to its home position (up). The package transfer slide 172 moves to its home position (under the package inserter 173). A magazine low sensor insures sufficient packages 170 are in the magazine 174. The slice feeder actuator 163 extends and slices a package 170 from the magazine 174. The package inserter 173 inserts a package 170 into the transfer slide 172 and the transfer slide 172 moves to present the package 170 to the needle loading area 171. All the foregoing actions are performed in sequence with end point control will be maintained via sensors, timers, or motion controller "move complete" signals.

Run Mode

Since there is a potential interference between the various components of the system 10 as they go through their associated range of motion, it is important that all motions of the components be coordinated by the controller 32 to insure that no collisions occur. During run mode, end point control is maintained by sensors, timers and motion controller "move complete" signals. Focusing first upon the needle transfer assembly 45, it can be noted that normally, the needle gripper fingers 58a–c are closed, each holding a needle 3 corresponding to a particular process step. In the right-most position (see FIG. 22), grippers units 56c and 56b will be retracted while gripper 56a will be extended. The needle transfer assembly 45 then moves all gripper units 56a–c to the next station in line (once it is safe to do so). When the needle transfer assembly 45 moves a swaged needle 3 and suture 7 combination (armed suture 2) from the swage station 92 to the pull test station 126 the suture transfer gripper 124 moves with it in synchronization, thus carrying the armed suture 2 under tension to the pull test station 126. Once the armed suture 2 is delivered to the pull test station 126, the suture transfer gripper 124 and needle gripper unit 56a open and retract. The suture transfer gripper 124 then moves back to a position in line with the suture tower assembly 66. The fingers 58a–c of needle gripper units 56a–c are all opened and the gripper unit is retracted when the processing stage, e.g., the precisor 78, receiving the needle 3 indicates that it has gripped it. After all the needles 3 have been deposited at their respective processing stages, 78, 42 and 126, the needle gripper units 56a–c retract and the gripper table 48 is moved to the right to the home position. After the processing stations 12,78,92,126,162 have performed their respective functions, all three gripper units 56a–c are extended and each gripper unit 56a–c will then close on the needles 3 present at the in-feed 12, precisor 78 and swage 92 assemblies (if needles are present). After the in-feed 12, precisor 78 and swage 92 release their respective needles 3, gripper units 56c and 56b will retract while gripper 56a remains extended.

In run mode, the needle precisor 78 performs the following actions in sequence. The precisor 78 waits for the needle transfer assembly 45 to present the next needle 3 for precising via needle gripper unit 56c. The precisor needle gripping fingers 80a, 80b close and wait for needle gripper fingers 58c to open and the needle gripper unit 56a to retract. The push block 82 then bumps the needle 3 into the desired position. The rotatable mount 88 rotates the delivered needle 3 to the proper orientation if needed as determined by cameras 28, 30. The push block 82 then retracts. The precisor 78 then waits for transfer gripper unit 56b to extend and needle gripping fingers 58b to close in preparation for carrying the needle 3 to the swaging station 92. The precisor needle gripping fingers 80a, 80b then open and needle gripper 56b retracts. The rotatable mount 88 then returns to its starting position, if necessary.

In Run Mode, the swaging station 92 performs the following actions in sequence. After the needle transfer assembly 45 moves an existing armed suture 2 from the swage station 92 to the pull test assembly 126 and delivers the next needle 3 to the swage assembly 92, the suture funnel portions 100, 102 close. Needle gripper unit 56b then extends to deliver a needle 3 to the swage opening 98. The swage assembly offset cylinder 123 is actuated and brings the swage assembly 92 down into swaging position. The preclamp cam 112 rotates to gently close the swage dies 94, 96 on the needle 3 and preclamp the needle 3. The suture transfer gripper 124 opens and retracts to the right. The suture 7 is then inserted into the suture hole 4 by the suture insertion gripper 70. The suture funnels 100, 102 are opened and the swaging cylinder 110 is activated to swage the needle 3. The system pauses until a swage pressure transducer indicates that the necessary swage pressure has been achieved. The suture insertion gripper 70 releases the suture and a suture detection sensor 165 verifies that the suture 7 has been attached (swaged) to the needle 3. The swage assembly 92 then waits for the needle gripper unit 56a to extend and for gripping fingers 58a to close on the needle 3 that has been swaged(if applicable). The swage cylinder 110 retracts to open the swage dies 94, 96. The swage assembly offset cylinder 123 then moves the entire swage assembly 92 up a short distance to clear the swage dies 94, 96 from the needle transfer path. The preclamp cam 112 then returns to its maximum interference position.

In Run Mode for single armed suture, the suture tower assembly 66 performs the following actions in sequence. Initially, the suture insertion gripper 70 is positioned behind the cutter 128 holding the free end of the suture 7 (ready for insertion). The suture transfer gripper 124 is positioned ahead of the cutter 128 and may or may not be closed on the suture remnant from the previous cycle (depending upon whether it was previously processing single or double armed sutures). The needle gripper unit 56a is extended and needle gripping fingers 58a are closed on the previously swaged needle held in the swage assembly 92. When the needle transfer assembly 45 moves needle gripper unit 56a from the swage assembly 92 to the pull test assembly 126, the suture transfer gripper 124 indexes to the pull test assembly 126 in a synchronized move. At the end of this move, the needle transfer assembly 45 delivers the next needle 3 to the swage station 92 via needle gripper unit 56b. The suture tower assembly 66 moves from its position behind the cutter 128 to a rest position, proximate to the swage station 92 after the needle and suture transfer gripper 124 have moved out of the way. The suture tower assembly 66 then waits until the next needle 3 has been preclamped by the swage dies 94, 96 and the needle gripping unit 56b is clear. The suture tower assembly 66 moves from the rest position to the insert position, i.e., to insert the suture 7 into the suture hole 4 of the needle 3 and waits for the swage assembly 92 to complete its swaging sequence. The suture insertion gripper 70 then opens and the suture tower assembly 66 moves the suture insertion gripper 70 to its position behind the cutter 128. The suture insertion gripper 70 then closes and waits until the suture transfer gripper 124 has delivered the previous needle/suture assembly 2 to the pull test assembly 126 and returns open to a position ahead of the cutter 128. The suture transfer gripper 124 then closes on the suture 7 and the suture cutter 128 cycles (close and open) to cut the suture 7.

Two insertion cycles are required to produce double-armed sutures 2. When making double-armed sutures 2, the suture transfer gripper 124 is not used. The suture tower assembly 66, cutter 128 and suture transfer gripper 124 perform the following actions in sequence.

First Insertion Cycle: (To Attach the First Needle 3a)

Initially, the suture insertion gripper 70 is positioned behind the cutter 128 holding the free end of the suture 7 ready for insertion into a needle 3a to be placed in the swage station 92. The suture transfer gripper 124 is open and positioned ahead of the cutter 128. The needle gripper unit 56a is extended and holding the previously swaged needle 3b, i.e., the second needle 3b of a previous double-armed suture 2. The suture transfer guide 60 is extended and supports a loop of suture 7 extending between the second needle 3b and the first needle 3a held in the pull test station 126. The needle transfer assembly 45 moves gripper unit 56a, holding the previously swaged needle 3b, from the swage assembly 92 to the pull test assembly 126, with needle gripper unit 56b, holding the first needle 3a of the next double armed suture 2 and moving it to the swaging assembly 92. The suture transfer guide 60 retracts after the pull test grippers 130, 132 have closed onto the needle 3b and suture 7 of the previously assembled double-armed suture 2. The suture tower 66 then moves from its position behind the cutter 128 to the rest position and waits there until the needle 3a of the new armed suture 2 has been delivered to and is preclamped in the swaging assembly 92. The suture tower 66 then moves the suture insert gripper 70 from the rest position to the insert position to insert the suture 7 which is gripped therein into the suture hole 4a of the needle 3a held in the swage station 92. The suture transfer gripper 124 is then positioned behind the cutter 128. The suture tower assembly 66 waits for the swage assembly 92 to complete swaging to attach the suture 7 to the needle 3a.

Simultaneously with the foregoing, the needle transfer assembly 45 has recycled and needle gripper unit 56a waits at the swaging station 92, to grasp the needle 3a, which has just been swaged. The suture transfer gripper 124 (positioned behind the cutter) closes to grasp the suture 7 and the suture insertion gripper 70 opens to release the suture 7 which should now be held in the needle 3a.

The suture detection sensor 165 determines if the suture 7 has been successfully attached to the needle 3a. If attachment is not detected during the first insertion cycle of a double armed suture sequence, the suture tower assembly 66 (and suture insertion gripper 70) will cut the length of suture that failed to attach as described below and repeat the first insertion cycle on subsequent needles until a successful attachment has been detected. When the suture detection sensor 165 shows that a suture has been attached, the suture tower assembly 66 moves the suture insertion gripper 70 to a position ahead of the cutter 128 and simultaneously rotates 180 degrees such that, the suture insertion gripper 70 faces rearwardly towards the cutter assembly 128. The suture insertion gripper 70 and suture loop gripper 72 both close. The cutter 128 cycles to cut the suture between the suture insertion gripper 70 and the suture transfer gripper 124, forming a free end that will be inserted into the next needle 3b. The suture transfer guide 60 is raised and engages the suture 7 (which will constitute the length extending between the attached needles 3a, 3b). If the suture detection sensor 165 shows that the suture 7 was not attached to the needle 3a in the swaging station 92, the suture transfer gripper 124 moves from behind to ahead of the cutter 128 (still holding the suture), and the suture tower assembly 66 moves the suture insertion gripper 70 to a position behind the cutter 128 and closes on the suture 7. The suture cutter 128 is activated to cut the suture 7. The suture transfer gripper 124 will then open and the segment of suture 7 that failed to attach is vacuumed from the system. The system then repeats a first insertion cycle, as described above.

Second Insertion Cycle:

The needle transfer assembly 45 moves needle gripping unit 56a from the swaging assembly 92 to the pull test assembly 126 and delivers a new needle 3b to the swaging assembly 92 via needle gripping unit 56b. The suture tower assembly 66 moves from its position ahead of the cutter 128 to the rest position. Simultaneously, the suture insertion gripper 70 rotates back 180 degrees (to face the swage assembly 92). The needle transfer assembly 45 movement and the suture tower assembly 66 movement must be synchronized to insure that the suture 7 is not stretched between needle gripping unit 56a and the suture tower grippers 70, 72. This synchronization is especially critical when assembling shorter length double-armed sutures 2, i.e., the grippers 70, 72 can not be rotated too quickly relative to the movement of the suture tower assembly 66 toward the swage station 92. The suture transfer gripper 124, which still holds a free end of the suture material 7 is then positioned forward of the cutter 128. The suture transfer guide 60 retracts after the pull test grippers 130, 132 have closed on the first insertion cycle needle 3a and suture 7 end. After the swaging assembly 92 has preclamped a second needle 3b, the suture tower assembly 66 moves the suture insertion gripper 70 from the rest position to the insert position, thereby inserting the suture 7 in the suture hole 4b, and waits for the swage assembly 92 to complete swaging. The suture insertion gripper 70 opens and the suture tower assembly 66 moves the suture insertion gripper 70 to a position behind the cutter 128. The suture insert gripper 70 closes and the suture cutter 128 is activated, cutting the suture 7 and then retracting. The suture transfer gripper 124 (positioned ahead of the cutter 128) opens and the waste suture remnant is vacuumed away, completing the second insertion cycle.

Considering now the run mode of the pull test assembly 126, it performs the following actions in sequence. The pull test assembly 126 waits until the needle transfer assembly 45 delivers an armed suture 2 via gripper unit 56a, which is extended to deliver needle 3a. When making single armed sutures, the suture transfer gripper 124 holds the end of the suture 7. The suture 7 is supported by the suture transfer guide 60 when making double-armed sutures 2. The pull test assembly needle gripper 130 then closes. Needle gripper unit 56a opens and retracts. If a minimum pull cycle is required, the following actions are taken: The first suture gripper 132 (minimum pull gripper) clamps onto the suture 7. The suture transfer gripper 124 then releases the suture 7 (single needle) or the suture transfer guide 60 retracts (double needle). The first suture gripper 132 then applies a fixed tension load to the suture 7. The tension load is maintained for 0.1 seconds. If the suture 7 separates from the needle 3 and fails to maintain the fixed tension load for 0.1 seconds or the first suture gripper 132 reaches a "bottom" position, the armed suture 2 will be treated as defective. If the minimum tension value is attained for 0.1 seconds and the first suture gripper 132 does not reach a "bottom" position, then the suture attachment will be considered as acceptable.

If a destructive pull test cycle is required, the following actions are taken: the second suture gripper 134 (destructive pull gripper) clamps onto the suture 7. The suture transfer gripper 124 releases the suture 7 (single needle) or the suture transfer guide 60 retracts (double needle). The second suture gripper 134 applies sufficient force to pull the suture 7 from the needle 3 at a controlled velocity. The peak force needed to separate the suture from the needle is recorded by the system controller 32. The peak force measurement may be used by the system controller 32 to adjust the position of the swage stop block 105, i.e., to optimize suture retention by optimal swage die 94, 96 control. The second suture gripper 134 is required to reach a "bottom" position or a "pull test assembly jam" message is generated. The suture attachment is marked as defective. After the minimum or destructive pull actions have been completed, the grippers 132,134 move to a "ready" position and open. The needle gripper 130 waits for the offload robot 35 to close its needle gripper fingers 42 on the needle 3 and then gripper 130 opens.

Upon the start of run mode, an empty package 170 is present at the needle loading area 171 ready for insertion of an armed suture 2. The needle gripper fingers 42 of robot 35 are closed and holding the needle 3 of an armed suture 2 at the pull test station 126. The pull test grippers 130,132,134 are clear. The following actions are then performed in sequence. The out-feed robot 35 moves away from the pull test assembly 126 to its "ready" position and sends an "OK to release needle" signal. The out-feed robot 35 places the needle 3 in a package 170, opens its gripper fingers 42, backs away, goes to its ready position and asserts a "Needle place complete" signal to the system controller 32. The output pick and place apparatus 180 retrieves the package 170 from the needle loading area 171. Once the full package 170 has been retrieved, the gripper on the pick and place gripper arm 184 retracts to its pick up position. The slice feed actuator 163 extends, pauses and retracts to deliver a package 170 to the package insertion actuator 173. The package insertion actuator 173 extends, pauses and retracts to deliver the previously sliced package 170 to the package transfer slide 172. The package transfer slide 172 actuates and moves the package 170 to the needle loading area 171. A package detect sensor verifies the presence of the package 170 at the load area. Once the pull test assembly 126 has completed its sequence, the system controller 32 asserts an "OK to pick needle" signal. The out-feed robot 35 sends a "Needle place complete" signal. The robot 35 moves to and, closes its grippers on the needle 3 held at the pull test station 126 and sends an "OK to release needle" signal to the system controller 32. The pull test station 126 opens its needle grippers 130. The system controller 32 sends an "OK to pick needle" signal and gripper 130 asserts a "Needle Released" signal. When double armed sutures 2 are being assembled, the controller 32 signals the robot 35 whether the first 3a or second 3b needle is being transferred and the package slice assembly 162 and the output pick and place unit 180 will cycle once after two "transfer" cycles. When the robot 35 picks a rejected needle 3, with or without suture 7, from the pull test gripper 126 as determined by a "no hook up" or "pull test failed" signals, the robot 35 drops the component(s) into a reject container and returns to its initial position. In this case, a new package 170 will not be fed by the slice feed station.

It should be understood that the embodiments described herein are merely exemplary and that a person skilled in the art may make many variations and modifications without departing from the spirit and scope of the invention as defined in the appended claims. All such variations and modifications are intended to be included within the scope of the present invention as defined in the appended claims.

We claim:

1. An apparatus for forming armed sutures, comprising:
   (A) a swaging station for receiving, holding and swaging needles that are deposited therein;
   (B) a suture insertion apparatus for inserting suture into needles held in said swaging station; said suture insertion apparatus acting along a straight first line and moving an end of the suture to be inserted along that line from a starting position to an ending position where the end of the suture is inserted in a suture hole of a needle;
   (C) a needle transfer assembly for carrying needles to and from the swaging station, said needle transfer assembly acting along a straight second line substantially perpendicular to said first line, said first line and said second line intersecting at said swaging station, said needle transfer assembly having a plurality of extensible needle grippers disposed on a base thereof, said base moveable along said second line to assume a plurality of positions wherein the plurality of needle grippers may be selectively aligned with and extended towards a plurality of needle processing stations including said swaging station for transferring needles to said plurality of needle processing stations, said base moveable through said plurality of positions and reciprocating to sequentially transfer a plurality of needles to said plurality of needle processing stations.

2. The apparatus of claim 1, wherein said suture insertion apparatus includes a suture insertion gripper mounted on a suture tower slideably driven on a linear motor.

3. The apparatus of claim 2, further comprising a suture payoff assembly for dispensing suture from a bulk supply thereof and a cutter for cutting the suture at predetermined lengths suitable for forming armed sutures, said cutter disposed adjacent to the suture between the swaging station and the suture payoff assembly.

4. The apparatus of claim 3, wherein said plurality of needle processing stations includes a precisor for establishing a precise position for a needle to be placed in the swaging station, said precisor disposed adjacent said swaging station, said needle transfer assembly having at least one needle gripper for transferring needles from said precisor to said swaging station.

5. The apparatus of claim 4, further including a suture transfer gripper moveable along the first line for grasping and moving the suture, said suture transfer gripper cooperating with said suture insertion gripper to hold the suture before and after cutting by said cutter, said suture transfer gripper moveable perpendicular to said first line.

6. The apparatus of claim 5, wherein said suture insertion gripper and said suture transfer gripper can pass each other when moving to control suture position.

7. The apparatus of claim 6, wherein said suture insertion gripper and said suture transfer gripper pass one another without colliding when one or the other is open.

8. The apparatus of claim 4, wherein the position and movement of the needle transfer assembly is controlled by a servo motor/screw driven slide.

9. The apparatus of claim 4, wherein said needle grippers extend and retract towards and away from the swaging station and the precisor.

10. The apparatus of claim 3, further including an inspection station between said swaging station and said payout station, said inspection station checking the condition of suture to avoid defects therein before attachment of the suture to a needle.

11. The apparatus of claim 3, wherein the cutter acts substantially at 90 degrees relative to the suture.

12. The apparatus of claim 2, further comprising a brake attached to the suture tower assembly to control the position thereof.

13. An apparatus for forming armed sutures, comprising:
   (A) a swaging station for receiving, holding and swaging needles that are deposited therein;
   (B) a suture insertion apparatus for inserting suture into needles held in said swaging station: said suture insertion apparatus acting alone a first line and moving an end of the suture to be inserted along that line from a starting position to an ending position where the end of the suture is inserted in a suture hole of a needle, said suture insertion apparatus including a suture insertion gripper mounted on a suture tower slideably driven on a linear motor, said insertion gripper being mounted on said suture tower via a rotatable turret, by which said suture insertion gripper may be oriented in a plurality of directions;
   (C) a needle transfer assembly for carrying needles to and from the swaging station, said needle transfer assembly acting along a second line substantially perpendicular to said first line, said first line and said second line intersecting at said swaging station;
   (D) a suture payoff assembly for dispensing suture from a bulk supply thereof;
   (E) a cutter for culling the suture at predetermined lengths suitable for forming armed sutures, said cutter disposed adjacent to the suture between the swaging station and the suture payoff assembly;
   (F) a precisor for establishing a precise position for a needle to be placed in the swaging station, said precisor disposed adjacent said swaging station, said needle transfer assembly having at least one needle gripper for transferring needles from said precisor to said swaging station; and
   (G) a suture transfer gripper moveable along the first line for grasping and moving the suture, said suture transfer gripper cooperating with said suture insertion gripper to hold the suture before and after cutting by said cutter.

14. The apparatus of claim 13, further comprising a loop gripper mounted on said rotatable turret distal to said suture insertion gripper in alignment therewith for simultaneously grasping suture disposed substantially along a line.

15. The apparatus of claim 14, further comprising a pull test station disposed adjacent said swaging station distal to said precisor, said pull test station, said swage station and said precisor being oriented beside one another along a line substantially parallel to said second line, said pull test station operable to pull the suture to test the attachment strength thereof to a needle.

16. The apparatus of claim 15, wherein said suture transfer gripper is disposed below the suture and is slideably mounted on a first platform to provide movement of said suture transfer gripper parallel to the first line.

17. The apparatus of claim 16, wherein said first platform is slideably mounted on a second platform to provide movement of said first platform in a direction perpendicular to said first line.

18. The apparatus of claim 17, further comprising swage die portions insertable within said swaging station to form a swage opening therebetween for receiving needles to be swaged and further comprising funnel portions insertable within said swage station to form a funnel opening, said funnel portions positionable over said die portions with the funnel opening substantially concentric with the swage opening to funnel a suture through said swage opening and into a suture hole in a needle held in said swage opening, said funnel portions moveable independently of said swage die portions.

19. The apparatus of claim 18, further comprising means for positioning said funnel portions with the funnel opening concentric with the swage opening to promote the insertion of suture in a needle hole of a needle held in the swage opening, and means for opening said funnel portions prior to swaging with the swaging die portions.

20. The apparatus of claim 19, further including means for opening the swage dies after swaging to allow the removal of a swaged needle.

21. The apparatus of claim 17, further including an indeed robot to retrieve a needle from a first surface and deliver the needle to a needle gripper of the needle transfer assembly.

22. The apparatus of claim 21, further including an outfeed robot to retrieve a needle from a needle gripper of the needle transfer assembly and and deliver it second surface.

23. The apparatus of claim 22, further including a packaging machine for delivering and retrieving packages proximate to the outfeed robot, said outfeed robot capable of placing needles into the packages delivered by said packaging machine.

24. The apparatus of claim 21, wherein said in feed robot has gripper fingers with radiused gripper pads, said gripper pads permitting said gripper fingers to grasp needles with different radii of curvature.

25. The apparatus of claim 17, wherein said at least one needle gripper on said needle transfer assembly is extensible and retractable in a direction parallel to the first line.

26. The apparatus of claim 16, wherein said second platform is slideably mounted on a third platform, said cutter also mounted upon the third platform, said second platform and said cutter thereby being displaceable along the first line to adjust the length of armed suture produced.

27. The apparatus of claim 26, wherein a blade of said cutter is disposed at an angle relative to the suture, such that a taper is formed on the cut end of the suture when it is cut by the cutter.

28. The apparatus of claim 27, wherein said cutter has a suture control arm that supports the suture when the cutter is cutting the suture, said suture control arm having a suture support notch therein to control the motion of the suture during cutting.

29. The apparatus of claim 28, where a support surface of said suture support notch is disposed at 90 degrees relative to the direction of blade travel.

30. The apparatus of claim 29, wherein said suture control arm has an angled slot therein communicating with the suture support notch, said angled slot permitting said blade to pass through said suture control arm to cut a suture supported in the suture support notch.

31. The apparatus of claim 15, wherein said at least one needle gripper includes a plurality of needle grippers, each mounted on the needle transfer assembly in a ganged arrangement to permit the simultaneous transfer of a plurality of needles by the plurality of needle grippers to a plurality of said swage station, said precisor and said pull test station.

32. The apparatus of claim 14, wherein said suture insertion gripper can assume a suture insertion position, a first hold position with the suture insertion gripper facing forward behind the suture transfer gripper for cutting suture to make single armed suture and a second hold position with the suture facing back ahead of the suture transfer gripper for cutting suture to make double armed sutures.

33. The apparatus of claim 13, wherein said suture insertion gripper has "L" shaped gripper fingers the bottom leg of the "L" extending parallel to the first line.

34. An apparatus for forming armed sutures, comprising:
(A) a swaging station for receiving, holding and swaging needles that are deposited therein;
(B) a suture insertion apparatus for inserting suture into needles held in said swaging station; said suture insertion apparatus acting along a first line and moving an end of the suture to be inserted along that line from a starting position to an ending position where the end of the suture is inserted in a suture hole of a needle, said suture insertion apparatus including a suture insertion gripper mounted on a suture tower slideably driven on a linear motor:
(C) a needle transfer assembly for carrying needles to and from the swaging station, said needle transfer assembly acting along a second line substantially; perpendicular to said first line, said first line and said second line intersecting at said swaging station;
(D) a suture payoff assembly for dispensing suture from a bulk supply thereof;
(E) a cutter for cutting the suture at predetermined lengths suitable for forming armed sutures, said cutter disposed adjacent to the suture between the swaging station and the suture payoff assembly;
(F) a precisor for establishing a precise position for a needle to be placed in the swaging station, said precisor disposed adjacent said swaging station, said precisor having a bump block for bumping against a blunt end of a needle inserted therein to control the depth of insertion of the needle in preparation for inserting the needle to a selected depth in the swaging station, said needle transfer assembly having at least one needle gripper for transferring needles from said precisor to said swaging station.

35. The apparatus of claim 34, wherein the position of said bump block is controlled be a micrometer adjustment.

36. An apparatus for forming armed sutures, comprising:
(A) a swaging station for receiving, holding and swaging needles that are deposited therein;
(B) a suture insertion apparatus for inserting suture into needles held in said swaging station; said suture insertion apparatus acting along a first line and moving an end of the suture to be inserted along that line from a starting position to an ending position where the end of the suture is inserted in a suture hole of a needle, said suture insertion apparatus including a suture insertion gripper mounted on a suture tower slideably driven on a linear motor;

(C) a needle transfer assembly for carrying needles to and from the swaging station, said needle transfer assembly acting along a second line substantially perpendicular to said first line, said first line and said second line intersecting at said swaging station;
(D) a suture payoff assembly for dispensing suture from a bulk supply thereof;
(E) a cutter for cutting the suture at predetermined lengths suitable for forming armed sutures, said cutter disposed adjacent to the suture between the swaging station and the suture payoff assembly;
(F) a precisor for establishing a precise position for a needle to be placed in the swaging station, said precisor disposed adjacent said swaging station, said precisor having a rotatable gripper to rotate the needle to position the curvature of the needle in a selected position for swaging, said needle transfer assembly having at least one needle gripper for transferring needles from said precisor to said swaging station.

37. A method for forming armed sutures, comprising the steps of:
   (A) receiving, holding and swaging needles in a swaging station;
   (B) prior to said step of swaging, inserting suture into a needle held in the swaging station via a suture insertion apparatus acting along a straight first line and moving an end of the suture to be inserted along the first line from a starting position to an ending position where the end of the suture is inserted in a suture hole of a needle; and
   (C) simultaneously carrying a plurality of needles to and from the swaging station with a needle transfer assembly having a plurality of extensible needle grippers disposed on a base thereof, by moving the base to assume a plurality of positions wherein the plurality of needle grippers are selectively aligned with a plurality of needle processing stations including the swaging station and extending the needle grippers toward the plurality of needle processing stations, said base moving and reciprocating through the plurality of positions to sequentially transfer a plurality of needles to the plurality of needle processing stations, the needle transfer assembly acting along a straight second line substantially perpendicular to the first line, the first line and the second line intersecting at the swaging station.

* * * * *